(12) United States Patent
Kruck et al.

(10) Patent No.: US 12,109,298 B2
(45) Date of Patent: Oct. 8, 2024

(54) IMPROVING THE FASTNESS TO WASHING OF PIGMENT-CONTAINING DYES BY USING AN OXIDATIVE PRETREATMENT AGENT

(71) Applicant: Henkel AG & Co. KGaA, Duesseldorf (DE)

(72) Inventors: Constanze Kruck, Grevenbroich (DE); Sandra Hilbig, Bochum (DE); Melanie Moch, Dormagen (DE); Daniela Kessler-Becker, Leverkusen (DE)

(73) Assignee: HENKEL AG & CO. KGAA, Duesseldorf, NY (US)

( * ) Notice: Subject to any disclaimer, the term of this patent is extended or adjusted under 35 U.S.C. 154(b) by 94 days.

(21) Appl. No.: 17/913,725

(22) PCT Filed: Feb. 1, 2021

(86) PCT No.: PCT/EP2021/052236
§ 371 (c)(1),
(2) Date: Sep. 22, 2022

(87) PCT Pub. No.: WO2021/190810
PCT Pub. Date: Sep. 30, 2021

(65) Prior Publication Data
US 2023/0099251 A1    Mar. 30, 2023

(30) Foreign Application Priority Data
Mar. 24, 2020  (DE) .......................... 102020203743.4

(51) Int. Cl.
| | |
|---|---|
| *A61Q 5/10* | (2006.01) |
| *A61K 8/22* | (2006.01) |
| *A61K 8/23* | (2006.01) |
| *A61K 8/25* | (2006.01) |
| *A61K 8/898* | (2006.01) |

(52) U.S. Cl.
CPC ............... *A61K 8/898* (2013.01); *A61K 8/22* (2013.01); *A61K 8/23* (2013.01); *A61K 8/25* (2013.01); *A61Q 5/10* (2013.01); *A61K 2800/4324* (2013.01); *A61K 2800/884* (2013.01)

(58) Field of Classification Search
CPC . A61K 8/898; A61K 8/22; A61K 8/23; A61K 8/25; A61K 2800/4324; A61K 2800/884; A61Q 5/10
USPC ........................................................... 8/405
See application file for complete search history.

(56) References Cited

U.S. PATENT DOCUMENTS

| | | | |
|---|---|---|---|
| 2013/0149358 A1* | 6/2013 | Colaco ................. | A61K 8/0254 424/70.6 |
| 2017/0157002 A1* | 6/2017 | Neuba ................. | A61K 8/4926 |
| 2017/0172901 A1 | 6/2017 | Kerl et al. | |

FOREIGN PATENT DOCUMENTS

| | | | | |
|---|---|---|---|---|
| DE | 102013226102 A1 * | 6/2015 | ............... | A61Q 5/04 |
| DE | 102014218006 A1 * | 3/2016 | ............... | A61Q 5/10 |
| EP | 2044977 A2 | 4/2009 | | |
| WO | WO 2017/108828 A1 * | 6/2017 | ............. | A61Q 5/065 |

* cited by examiner

*Primary Examiner* — Eisa B Elhilo
(74) *Attorney, Agent, or Firm* — Lorenz & Kopf, LLP

(57) ABSTRACT

A process and a kit-of-parts for dyeing keratinous material, in particular human hair, are provided. An exemplary process includes applying a pre-treatment agent (V) to the keratinous material, wherein the pre-treatment agent in a cosmetic carrier includes at least one oxidizing agent (V-1), and applying a colorant (F) to the keratinous material, the colorant being in a cosmetic carrier and including (F-1) at least one amino-functionalized silicone polymer and (F-2) at least one pigment.

20 Claims, No Drawings

IMPROVING THE FASTNESS TO WASHING OF PIGMENT-CONTAINING DYES BY USING AN OXIDATIVE PRETREATMENT AGENT

CROSS-REFERENCE TO RELATED APPLICATION

This application is a U.S. National-Stage entry under 35 U.S.C. § 371 based on International Application No. PCT/EP2021/052236, filed Feb. 1, 2021, which was published under PCT Article 21(2) and which claims priority to German Application No. 102020203743.4, filed Mar. 24, 2020, which are all hereby incorporated in their entirety by reference.

TECHNICAL FIELD

The subject of the present application is a cosmetic process for coloring keratinous material, in particular human hair, which comprises the application of at least two different agents (V) and (F). The agent (V) represents a pretreatment agent comprising at least one oxidizing agent in a cosmetic carrier. The colorant (F) comprises, in a cosmetic carrier, at least one amino-functionalized silicone polymer (F-1) and at least one pigment (F-2).

A second subject of this application is a multi-component packaging unit (kit-of-parts) for dyeing keratinous material, in particular human hair, which comprises the two agents (V) and (F) separately assembled in two different containers.

A third subject of this application is the use of the previously described colorant (F) for coloring oxidative pretreated human hair.

BACKGROUND

Changing the shape and color of keratinous material, especially human hair, is an important area of modern cosmetics. To change the hair color, the expert knows various coloring systems depending on the coloring requirements. Oxidation dyes are usually used for permanent, intensive dyeing with good fastness properties and good grey coverage. Such colorants contain oxidation dye precursors, so-called developer components and coupler components, which, under the influence of oxidizing agents such as hydrogen peroxide, form the actual dyes among themselves. Oxidation dyes are exemplified by very long-lasting dyeing results.

When direct dyes are used, ready-made dyes diffuse from the colorant into the hair fiber. Compared to oxidative hair dyeing, the dyeing obtained with direct dyes have a shorter shelf life and quicker wash ability. Dyes with direct dyes usually remain on the hair for a period of between 5 and 20 washes.

The use of color pigments is known for short-term color changes on the hair and/or skin. Color pigments are generally understood to be insoluble, coloring substances. These are present undissolved in the dye formulation in the form of small particles and are only deposited from the outside on the hair fibers and/or the skin surface. Therefore, they can usually be removed again without residue by a few washes with detergents comprising surfactants. Various products of this type are available on the market under the name hair mascara.

If the user wants particularly long-lasting dyeing, the use of oxidative dyes has so far been his/her only option. However, despite numerous optimization attempts, an unpleasant ammonia or amine odor cannot be completely avoided in oxidative hair dyeing. The hair damage still associated with the use of oxidative dyes also has a negative effect on the user's hair. A continuing challenge is therefore the search for alternative, high-performance dyeing processes. One possible alternative coloring system that has recently come increasingly into focus is based on the use of colored pigments.

Coloring with pigments offers several significant advantages. Since the pigments merely attach themselves to the keratin materials from the outside, in particular to the hair fibers, colorations that are no longer desired can be removed quickly and easily without leaving any residue, thus offering the user the possibility of returning to his original hair color immediately and without great effort. Especially for those consumers who do not want to recolor their hair regularly, this coloring process is therefore particularly attractive.

In recent work, the problem of low durability of this staining system has been addressed. In this context, it was found that the wash fastness of the color results obtained with pigments could be greatly improved by combining the pigments with certain amino-functionalized silicone polymers. In addition, by selecting particularly well-suited pigments and pigment concentrations on dark hair, it was possible to achieve a lighter color result, so that with this coloring system it was even possible to lighten hair, which until then had only been possible with oxidative hair treatment agents (bleaching or blonding agents).

BRIEF SUMMARY

A process for dyeing keratinous material, in particular human hair, is provided and includes applying a pre-treatment agent (V) to the keratinous material, wherein the pre-treatment agent in a cosmetic carrier includes at least one oxidizing agent (V-1), and applying a colorant (F) to the keratinous material, the colorant being in a cosmetic carrier and including (F-1) at least one amino-functionalized silicone polymer and (F-2) at least one pigment.

A kit-of-parts for dyeing keratinous material is provided and includes, separately packaged, a first container including a pretreatment agent (V), the pretreatment agent including at least one oxidizing agent (V-1), and a second container including a colorant (F), the colorant being in a cosmetic carrier and including (F-1) at least one amino-functionalized silicone polymer and (F-2) at least one pigment.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

In addition to these many advantages, however, the pigment-based coloring system still has some disadvantages, which are due to the low penetration depth of the pigments into the keratinic material. Since the pigments do not diffuse into the keratin material or keratin fiber, but are merely deposited in the form of a shell or film on the outside of the keratin material, the wash fastness of the dyeing produced with this system still requires improvement. Even though a good improvement in wash fastness has already been achieved by selecting particularly well-suited pigments or amino silicones, this still cannot be described as optimal.

It was therefore the task of the present application to find a pigment-based dyeing process with which intensive dyeing with improved fastness to washing can be achieved. In this context, the keratin materials or, in particular, hair dyed with this process should provide coloration in exactly the shade and intensity that the user expects after reading the relevant packaging information or instructions for use, irrespective of the hair type and other cosmetic products previously used. Even after a long period of time and several hair washes, there should be no unwanted shifts in the nuances of the dyed hair.

Surprisingly, it has now been found that the wash fastness of pigment-dyeing systems can be greatly improved if keratinic materials, especially hair, are subjected to oxidative pretreatment before the actual dyeing process.

A first object of the present disclosure is a method for coloring keratinous material, in particular human hair, comprising the following steps:

Application of a pre-treatment agent (V) to the keratinous material, wherein the pre-treatment agent in a cosmetic carrier is
 (V-1) comprises at least one oxidizing agent, and
Application of a colorant (F) to the keratinous material, the colorant being in a cosmetic carrier
 (F-1) at least one amino-functionalized silicone polymer and
 (F-2) comprises at least one pigment.

In the work leading to the present disclosure, it has been shown that particularly intense and wash fast color results can be obtained on hair when the hair has been colored by successive application of the two agents (V) and (F). Here, even after several hair washes, no undesirable or unattractive nuance shift occurred.

Keratinic Material

Keratinous material includes hair, skin, nails (such as fingernails and/or toenails). Wool, furs and feathers also fall under the definition of keratinous material. Preferably, keratinous material is understood to be human hair, human skin and human nails, especially fingernails and toenails. Keratinous material is understood to be human hair in particular.

Coloring Agent

The term "coloring agent" is used in the context of this present disclosure for a coloring of the keratin material, in particular the hair, caused by the use of pigments. In this coloring process, the pigments are deposited as coloring compounds in a particularly homogeneous, uniform and smooth film on the surface of the keratin material.

Pretreatment Agent (V)

In the process as contemplated herein, the pretreatment agent (V) is applied to the keratinous materials, in particular to the keratin fibers, prior to application of the colorant (F).

Cosmetic Carrier of the Pretreatment Agent (V)

The pretreatment agent (V) is characterized in that it comprises at least one oxidizing agent (V-1) in a cosmetic carrier.

For example, a suitable aqueous, alcoholic or aqueous-alcoholic carrier can be used as a cosmetic carrier for the pretreatment agent (V). For the purpose of hair coloring, such carriers are, for example, creams, emulsions, gels, pastes or also surfactant-comprising foaming solutions, such as shampoos, foam aerosols, foam formulations or other preparations suitable for application to the hair.

If the pretreatment agent (V) comprises the oxidizing agent(s) in an aqueous or water-comprising carrier, the pretreatment agent (V) preferably has an average water content. It has been found that particularly well suited for use in the process as contemplated herein are those pretreatment agents (V) which—based on the total weight of the pretreatment agent (V)—contain 30.0 to 80.0 wt. %, preferably 35.0 to 80.0 wt. %, further preferably 40.0 to 70.0 wt. % and very particularly preferably 45.0 to 60.0 wt. % water.

In one embodiment, a process as contemplated herein is characterized in that the pretreatment agent (V) comprises—based on the total weight of the pretreatment agent (V)—30.0 to 80.0 wt. %, preferably 35.0 to 80.0 wt. %, further preferably 40.0 to 70.0 wt. % and very particularly preferably 45.0 to 60.0 wt. % water.

Oxidizing Agent (V-1) or (V-2) in the Pretreatment Agent (V)

Oxidizing agents are substances that have an oxidizing effect. The oxidizing agents according to the present disclosure are particularly capable of oxidative modifying the keratin material or the human hair. The oxidizing agents as contemplated herein are different from atmospheric oxygen and have such an oxidation potential that allows disulfide bridges to be established within or between the proteins of the hair keratin and the natural color pigment melanin to be oxidative lightened.

In the context of one embodiment, hydrogen peroxide and/or at least one addition product thereof, in particular to inorganic or organic compounds, such as, for example, sodium perborate, sodium percarbonate, magnesium percarbonate, sodium percarbamide, polyvinylpyrrolidone.n $H_2O_2$ (n is a positive integer greater than 0), urea peroxide and melamine peroxide are particularly preferred oxidizing agents.

In a further embodiment, persulfates and/or their salts can also be used as oxidizing agents in the pretreatment agent (V). The use of one or more persulfates from the group consisting of ammonium peroxodisulfate, potassium peroxodisulfate and sodium peroxodisulfate is particularly preferred.

Ammonium peroxodisulfate, which may alternatively also be referred to as ammonium persulfate, is understood as meaning the persulfate having the empirical formula $(NH_4)_2S_2O_8$.

Potassium peroxodisulfate, which can alternatively also be referred to as potassium peruslfate, is understood as meaning the persulfate having the empirical formula $K_2S_2O_8$.

Sodium peroxodisulfate, which may alternatively also be referred to as sodium persulfate, is understood as meaning persulfate having the empirical formula $Na_2S_2O_8$.

In a very particularly preferred embodiment, a process as contemplated herein is characterized in that the pretreatment agent (V) comprises at least one oxidizing agent (V-1) selected from the group consisting of hydrogen peroxide, ammonium peroxodisulfate, potassium peroxodisulfate and sodium peroxodisulfate.

In carrying out the tests leading to the present disclosure, it was found that a strong and effective improvement in wash fastness could be achieved in particular when a pretreatment agent (V) comprising a combination of different oxidizing agents was used in the process as contemplated herein. Particularly good results were obtained when using a pretreatment agent (V) comprising the combination of hydrogen peroxide (V-1) and at least one persulfate (V-2) selected from the group consisting of ammonium peroxodisulfate, potassium peroxodisulfate and sodium peroxodisulfate.

In the context of a further very particularly preferred embodiment, a process as contemplated herein is characterized in that the pretreatment agent (V) comprises
 (V-1) hydrogen peroxide and (V-2) at least one persulfate selected from the group consisting of ammonium peroxodisulfate, potassium peroxodisulfate and sodium peroxodisulfate.

In the context of a further very particularly preferred embodiment, a process as contemplated herein is characterized in that the pretreatment agent (V) comprises
(V-1) hydrogen peroxide and
(V-2) Ammonium peroxodisulfate.

In the context of a further very particularly preferred embodiment, a process as contemplated herein is characterized in that the pretreatment agent (V) comprises
(V-1) hydrogen peroxide and
(V-2) Potassium peroxodisulfate.

In the context of a further very particularly preferred embodiment, a process as contemplated herein is characterized in that the pretreatment agent (V) comprises
(V-1) hydrogen peroxide and
(V-2) Sodium peroxodisulfate.

In the context of a further very particularly preferred embodiment, a process as contemplated herein is characterized in that the pretreatment agent (V) comprises
(V-1) hydrogen peroxide and
(V-2) Ammonium peroxodisulfate and potassium peroxodisulfate.

In the context of a further very particularly preferred embodiment, a process as contemplated herein is characterized in that the pretreatment agent (V) comprises
(V-1) hydrogen peroxide and
(V-2) ammonium peroxodisulfate and sodium peroxodisulfate.

In the context of a further very particularly preferred embodiment, a process as contemplated herein is characterized in that the pretreatment agent (V) comprises
(V-1) hydrogen peroxide and
(V-2) potassium peroxodisulfate and sodium peroxodisulfate.

In the context of a further very particularly preferred embodiment, a process as contemplated herein is characterized in that the pretreatment agent (V) comprises
(V-1) hydrogen peroxide and
(V-2) Ammonium peroxodisulfate and potassium peroxodisulfate and sodium peroxodisulfate.

As contemplated herein, the oxidative cosmetic pretreatment agent may also additionally contain at least one catalyst as an optional component that activates the oxidation of the substrate, such as the melanin present in the keratin material. Such catalysts include metal ions, iodides, quinones, or certain enzymes.

Suitable metal ions are, for example, $Zn^{2+}$, $Cu^{2+}$, $Fe^{2+}$, $Fe^{3+}$, $Mn^{2+}$, $Mn^{4+}$, $Li^+$, $Mg^{2+}$, $Ca^{2+}$ and $Al^{3+}$. $Zn^{2+}$, $Cu^{2+}$ and $Mn^{2+}$ are particularly suitable. In principle, the metal ions can be used in the form of any physiologically acceptable salt or in the form of a complex compound. Preferred salts are the acetates, sulfates, halides, lactates and tartrates.

Suitable enzymes include peroxidases, which can significantly enhance the effect of small amounts of hydrogen peroxide. Furthermore, such enzymes are suitable as contemplated herein which generate small amounts of hydrogen peroxide in situ with the aid of atmospheric oxygen and in this way biocatalytically activate the oxidation of the dye precursors. Particularly suitable catalysts for the oxidation of dye precursors are the so-called 2-electron oxidoreductases in combination with the specific substrates for this purpose, e.g.
Pyranose oxidase and e.g. D-glucose or galactose,
Glucose oxidase and D-glucose,
Glycerol oxidase and glycerol,
Pyruvate oxidase and benzoprovic acid or their salts;
Alcohol oxidase and alcohol (MeOH, EtOH),
Lactate oxidase and lactic acid and their salts,
Tyrosinase oxidase and tyrosine,
Uricase and uric acid or their salts,
Choline oxidase and choline,
Amino acid oxidase and amino acids.

By selecting the appropriate ranges of amounts of oxidizing agent(s) (V-1) (or (V-1) and (V-2)) in the pretreatment agent (V), the magnitude of the influence that the pretreatment agent (V) has on the fastness to washing of the subsequently applied colorant (F) can be specifically controlled. In this context, it has been found that the higher the amount of oxidant(s) used in the pretreatment agent (V), the better the wash fastness. On the other hand, however, the damage to the keratin material or keratin fibers/hairs also increases with an increase in the amount of oxidizing agents used. In order to find the optimum balance between these two effects, it has proved particularly preferable to use the oxidizing agent(s) in very specific quantity ranges in the pretreatment agent.

Preferably, the pretreatment agent as contemplated herein comprises—based on the total weight of the pretreatment agent—0.1 to 12.0 wt. %, further preferably 0.5 to 10.0 wt. %, still further preferably 1.5 to 8.0 wt. % and very particularly preferably 3.0 to 6.0 wt. % hydrogen peroxide (V-1).

In the context of a further very particularly preferred embodiment, a process as contemplated herein is characterized in that the pretreatment agent (V)—based on the total weight of the pretreatment agent—comprises (V-1) 0.1 to 12.0 wt. % preferably 0.5 to 10.0 wt. %, further preferably 1.5 to 8.0 wt. % and very particularly preferably 3.0 to 6.0 wt. % hydrogen peroxide.

Preferably, the pretreatment agent (V) as contemplated herein comprises—based on the total weight of the pretreatment agent—one or more persulfates (V-2) from the group consisting of ammonium peroxodisulfate, potassium peroxodisulfate and sodium peroxodisulfate in a total amount of from 5.0 to 30.0 wt. %, more preferably from 8.0 to 27.0 wt. %, still more preferably from 11.0 to 24.0 wt. % and very particularly from 14.0 to 21.0 wt. %.

In another particularly preferred embodiment, a process as contemplated herein is characterized in that the pretreatment agent (V)—based on the total weight of the pretreatment agent—(V2) comprises one or more persulfates selected from the group consisting of ammonium peroxodisulfate, potassium peroxodisulfate and sodium peroxodisulfate in a total amount of from 5.0 to 30.0 wt. %, preferably from 8.0 to 27.0 wt. %, more preferably from 11.0 to 24.0 wt. % and most preferably from 14.0 to 21.0 wt. %.

Coloring Agent (F)

Following the application of the pretreatment agent (V), the colorant (F) is now applied to the keratin material in the process as contemplated herein.

Cosmetic Carrier of The Colorant (F)

The colorant (F) comprises at least one amino-functionalized silicone polymer (F-1) and at least one pigment (F-2) in a cosmetic carrier.

For example, a suitable aqueous, alcoholic or aqueous-alcoholic carrier can be used as the cosmetic carrier for the colorant (F). For the purpose of hair coloring, such carriers are, for example, creams, emulsions, gels, pastes or also surfactant-comprising foaming solutions, such as shampoos, foam aerosols, foam formulations or other preparations suitable for application to the hair.

If the colorant (F) comprises the amino-functionalized silicone polymer(s) (F-1) and the pigment(s) (F-2) in an aqueous or water-comprising carrier, the colorant (F) preferably has a high water content. It has been found that particularly well suited for use in the process as contemplated herein are colorants (F) which—based on the total weight of the pretreatment agent (V)—contain 50.0 to 99.0 wt. %, preferably 60.0 to 99.0 wt. %, further preferably 70.0 to 99.0 wt. % and very particularly preferably 80.0 to 99.0 wt. % water.

In one embodiment, a process as contemplated herein is characterized in that the colorant (F) comprises—based on the total weight of the colorant (F)—50.0 to 99.0 wt. %, preferably 60.0 to 99.0 wt. %, further preferably 70.0 to 99.0 wt. % and very particularly preferably 80.0 to 99.0 wt. % water.

Amino Functionalized Silicone Polymer (F-1) in Colorant (F)

As the first ingredient (F-1) essential to the present disclosure, the colorant (F) comprises at least one amino-functionalized silicone polymer. The amino-functionalized silicone polymer may alternatively be referred to as amino silicone or amodimethicone.

Silicone polymers are generally macromolecules with a molecular weight of at least 500 g/mol, preferably at least 1000 g/mol, more preferably at least 2500 g/mol, particularly preferably at least 5000 g/mol, which comprise repeating organic units.

The maximum molecular weight of the silicone polymer depends on the degree of polymerization (number of polymerized monomers) and the batch size, and is partly determined by the polymerization method. For the purposes of the present disclosure, it is preferred if the maximum molecular weight of the silicone polymer is not more than $10^7$ g/mol, preferably not more than $10^6$ g/mol, and particularly preferably not more than $10^5$ g/mol.

The silicone polymers comprise many Si—O repeating units, and the Si atoms may carry organic radicals such as alkyl groups or substituted alkyl groups. Alternatively, a silicone polymer is therefore also referred to as polydimethylsiloxane or a derivative thereof Corresponding to the high molecular weight of silicone polymers, these are based on more than 10 Si—O repeat units, preferably more than 50 Si—O repeat units, and more preferably more than 100 Si—O repeat units, most preferably more than 500 Si—O repeat units.

An amino-functionalized silicone polymer is understood to be a functionalized silicone that carries at least one structural unit with an amino group. Preferably, the amino-functionalized silicone polymer carries multiple structural units, each having at least one amino group. An amino group is understood to mean a primary amino group, a secondary amino group and a tertiary amino group. All these amino groups can be protonated in the acidic environment and are then present in their cationic form.

In principle, good effects could be obtained with amino-functionalized silicone polymers (F-1) if they carry at least one primary, at least one secondary and/or at least one tertiary amino group. However, dyeing with the best wash fastness were observed when an amino-functionalized silicone polymer (F-1) comprising at least one secondary amino group was used in the dye (F).

In a very particularly preferred embodiment, a process as contemplated herein is characterized in that the colorant (F) comprises at least one amino-functionalized silicone polymer (F-1) having at least one secondary amino group.

The secondary amino group(s) may be located at various positions on the amino-functionalized silicone polymer. Particularly good effects were found when an amino-functionalized silicone polymer (F-1) was used that has at least one, preferably several, structural units of the formula (Si amino).

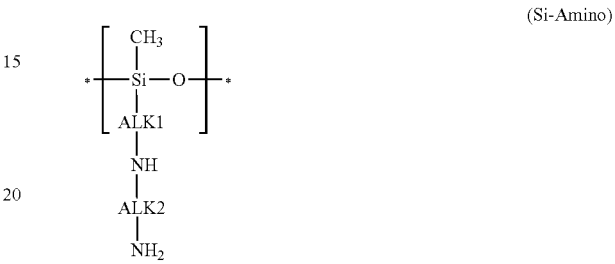

(Si-Amino)

In the structural units of the formula (Si-Amino), the abbreviations ALK1 and ALK2 independently represent a linear or branched, divalent $C_1$-$C_{20}$ alkylene group.

In another very particularly preferred embodiment, a process as contemplated herein is characterized in that the colorant (F) comprises at least one amino-functionalized silicone polymer (F-1) comprising at least one structural unit of the formula (Si-Amino),

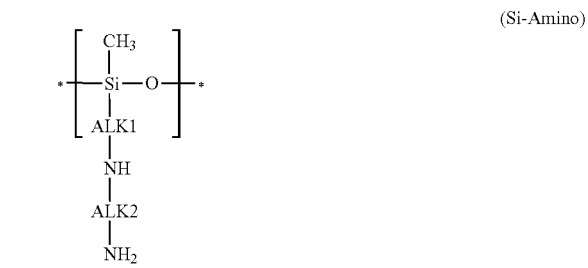

(Si-Amino)

where
ALK1 and ALK2 independently represent a linear or branched $C_1$-$C_{20}$ divalent alkylene group.

The positions marked with an asterisk (*) indicate the bond to further structural units of the silicone polymer. For example, the silicon atom adjacent to the star may be bonded to another oxygen atom, and the oxygen atom adjacent to the star may be bonded to another silicon atom or even to a $C_1$-$C_6$ alkyl group.

A bivalent $C_1$-$C_{20}$ alkylene group can alternatively be referred to as a divalent or divalent $C_1$-$C_{20}$ alkylene group, by which is meant that each ALK1 or AK2 grouping can form two bonds.

In the case of ALK1, one bond occurs from the silicon atom to the ALK1 grouping, and the second bond is between ALK1 and the secondary amino group.

In the case of ALK2, one bond is from the secondary amino group to the ALK2 grouping, and the second bond is between ALK2 and the primary amino group.

Examples of a linear bivalent $C_1$-$C_{20}$ alkylene group include the methylene group (—$CH_2$—), the ethylene group (—$CH_2$—$CH_2$—), the propylene group (—$CH_2$—$CH_2$—

$CH_2$—), and the butylene group (—$CH_2$—$CH_2$—$CH_2$—$CH_2$—). The propylene group (—$CH_2$—$CH_2$—$CH_2$—) is particularly preferred. From a chain length of 3 C atoms, bivalent alkylene groups can also be branched. Examples of branched divalent, bivalent $C_3$-$C_{20}$ alkylene groups are (—$CH_2$—$CH(CH_3)$—) and (—$CH_2$—$CH(CH_3)$—$CH_2$—).

In another particularly preferred embodiment, the structural units of the formula (Si amino) represent repeat units in the amino-functionalized silicone polymer (F-1), so that the silicone polymer comprises multiple structural units of the formula (Si amino).

Particularly well-suited amino-functionalized silicone polymers (F-1) with at least one secondary amino group are listed below.

Dyeing with the very best wash fastnesses could be obtained if in the process as contemplated herein at least one dyeing agent (F) was applied to the keratinous material which comprises at least one amino-functionalized silicone polymer (F-1) comprising structural units of the formula (Si-I) and of the formula (Si-II)

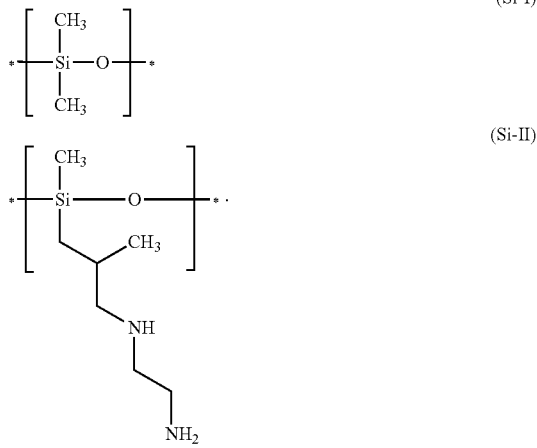

In a further explicitly quite particularly preferred embodiment, a process as contemplated herein is characterized in that the colorant (F) comprises at least one amino-functionalized silicone polymer (F-1) which comprises structural units of the formula (Si-I) and of the formula (Si-II)

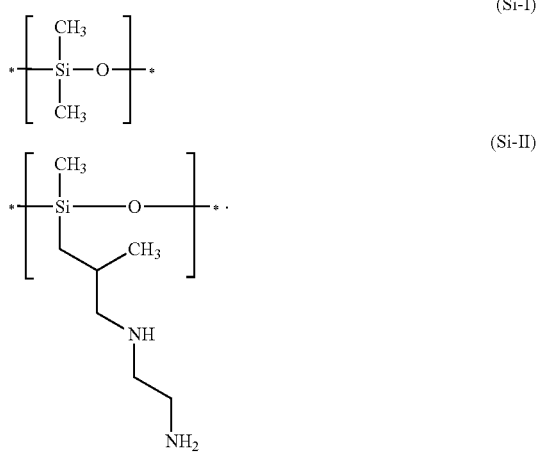

A corresponding amino-functionalized silicone polymer with the structural units (Si-I) and (Si-II) is, for example, the commercial product DC 2-8566 or Dowsil 2-8566 Amino Fluid, which is commercially distributed by the Dow Chemical Company and bears the designation "Siloxanes and Silicones, 3-[(2-aminoethyl)amino]-2-methylpropyl Me, Di-Me-Siloxane" and the CAS number 106842-44-8. Another particularly preferred commercial product is Dowsil AP-8658 Amino Fluid, which is also sold commercially by the Dow Chemical Company.

In the context of a further preferred embodiment, a process as contemplated herein is exemplified by the application of a colorant (F) to the keratinous material, the colorant (F) comprising at least one amino-functional silicone polymer (F-1) of the formula of formula (Si-III),

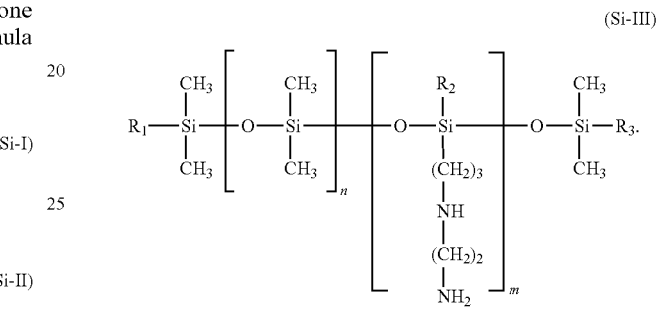

where
m and n mean numbers chosen so that the sum (n+m) is in the range 1 to 1000,
n is a number in the range 0 to 999 and m is a number in the range 1 to 1000,
R1, R2 and R3, which are the same or different, denote a hydroxy group or a C1-4 alkoxy group,
wherein at least one of R1 to R3 represents a hydroxy group;

Other processes preferred as contemplated herein are exemplified by the application of a colorant (F) to the keratinous material, the colorant (F) comprising at least amino-functional silicone polymer (F-1) of the formula of formula (Si-IV),

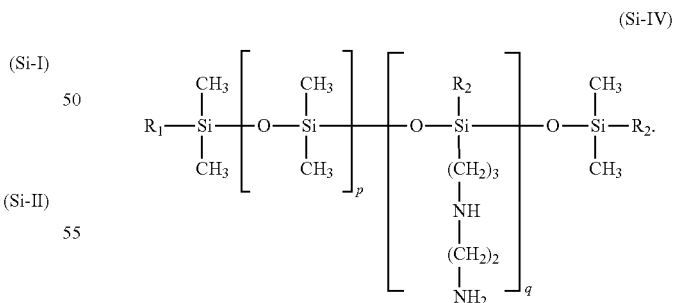

located in the
p and q mean numbers chosen so that the sum (p+q) is in the range 1 to 1000,
p is a number in the range 0 to 999 and q is a number in the range 1 to 1000,
R1 and R2, which are different, denote a hydroxy group or a C1-4 alkoxy group, at least one of R1 to R2 denoting a hydroxy group.

The silicones of the formulas (Si-III) and (Si-IV) differ in the grouping at the Si atom, which carries the nitrogen-comprising group: In formula (Si-III), R2 represents a hydroxy group or a C1-4 alkoxy group, while the radical in formula (Si-IV) is a methyl group. The individual Si groupings, which are marked with the indices m and n or p and q, do not have to be present as blocks; rather, the individual units can also be present in a statistically distributed manner, i.e. in the formulas (Si-III) and (Si-IV), not every R1-Si(CH$_3$)$_2$ group is necessarily bonded to an —[O—Si(CH$_3$)$_2$] grouping.

Processes as contemplated herein in which a colorant (F) comprising at least one amino-functional silicone polymer (F-1) of formula (Si-V) is applied to the keratin fibers have also proved to be particularly effective with respect to the desired effects.

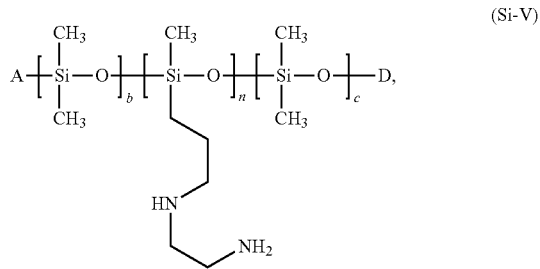

(Si-V)

located in the

A represents a group —OH, —O—Si(CH$_3$)$_3$, —O—Si(CH$_3$)$_2$OH , —O—Si(CH$_3$)$_2$OCH$_3$, D represents a group —H, —Si(CH$_3$)$_3$, —Si(CH$_3$)$_2$OH, —Si(CH$_3$)$_2$OCH$_3$, b, n and c stand for integers between 0 and 1000, with the specifications n>0 and b+c>0 at least one of the conditions A= —OH or D= —H is fulfilled.

In the above formula (Si-V), the individual siloxane units are statistically distributed with the indices b, c and n, i.e. they do not necessarily have to be block copolymers.

The colorant (F) may further comprise one or more different amino-functionalized silicone polymers represented by the formula (Si-VI)

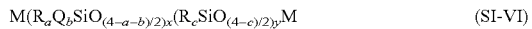

(SI-VI)

in which formula above R is a hydrocarbon or a hydrocarbon radical having from 1 to about 6 carbon atoms, Q is a polar radical of the general formula —R$^1$HZ wherein R$^1$ is a divalent linking group bonded to hydrogen and the radical Z composed of carbon and hydrogen atoms, carbon, hydrogen and oxygen atoms, or carbon, hydrogen and nitrogen atoms, and Z is an organic amino functional radical comprising at least one amino functional group; "a" takes values ranging from about 0 to about 2, "b" takes values ranging from about 1 to about 3, "a"+"b" is less than or equal to 3, and "c" is a number ranging from about 1 to about 3, and x is a number ranging from 1 to about 2.000, preferably from about 3 to about 50 and most preferably from about 3 to about 25, and y is a number in the range of from about 20 to about 10,000, preferably from about 125 to about 10,000 and most preferably from about 150 to about 1,000, and M is a suitable silicone end group as known in the prior art, preferably trimethylsiloxy. Non-limiting examples of radicals represented by R include alkyl radicals, such as methyl, ethyl, propyl, isopropyl, isopropyl, butyl, isobutyl, amyl, isoamyl, hexyl, isohexyl and the like; alkenyl radicals, such as vinyl, halovinyl, alkylvinyl, allyl, haloallyl, alkylallyl; cycloalkyl radicals, such as cyclobutyl, cyclopentyl, cyclohexyl and the like; phenyl radicals, benzyl radicals, halohydrocarbon radicals, such as 3- chloropropyl, 4-bromobutyl, 3,3,3-trifluoropropyl, chlorocyclohexyl, bromophenyl, chlorophenyl and the like, and sulfur-comprising radicals, such as mercaptoethyl, mercaptopropyl, mercaptohexyl, mercaptophenyl and the like; preferably R is an alkyl radical comprising from 1 to about 6 carbon atoms, and most preferably R is methyl. Examples of R$^1$ include methylene, ethylene, propylene, hexamethylene, decamethylene, —CH$_2$CH(CH$_3$)CH$_2$—, phenylene, naphthylene, —CH$_2$CH$_2$SCH$_2$CH$_2$—, —CH$_2$CH$_2$OCH$_2$—, —OCH$_2$CH$_2$—, —OCH$_2$ CH$_2$CH$_2$, —CH$_2$CH(CH$_3$)C(O)OCH$_2$—, —(CH$_2$)$_3$ CC(O) OCH$_2$CH$_2$—, —C$_6$H$_4$C$_6$H$_4$—, —C$_6$H$_4$CH$_2$C$_6$H$_4$—; and —(CH$_2$)$_3$C(O)SCH$_2$CH$_2$—.

Z is an organic amino functional radical comprising at least one amino functional group. One possible formula for Z is NH(CH$_2$)$_z$NH$_2$, where z is 1 or more. Another possible formula for Z is —NH(CH$_2$)$_z$(CH$_2$)$_{zz}$NH, wherein both z and zz are independently 1 or more, this structure comprising diamino ring structures, such as piperazinyl. Z is most preferably an —NHCH$_2$CH$_2$NH$_2$ radical. Another possible formula for Z is —N(CH$_2$)$_z$(CH$_2$)$_{zz}$NX$_2$ or —NX$_2$, wherein each X of X$_2$ is independently selected from the group consisting of hydrogen and alkyl groups having 1 to 12 carbon atoms, and zz is 0.

Q is most preferably a polar, amine-functional radical of the formula —CH$_2$CH$_2$CH$_2$NHCH$_2$CH$_2$NH$_2$. In the formulas, "a" takes values ranging from about 0 to about 2, "b" takes values ranging from about 2 to about 3, "a"+"b" is less than or equal to 3, and "c" is a number ranging from about 1 to about 3. The molar ratio of R$_a$Q$_b$ SiO$_{(4-a-b)/2}$ units to R$_c$SiO$_{(4-c)/2}$ units is in the range of about 1:2 to 1:65, preferably from about 1:5 to about 1:65 and most preferably by about 1:15 to about 1:20. If one or more silicones of the above formula are used, then the various variable substituents in the above formula may be different for the various silicone components present in the silicone mixture.

In a particularly preferred embodiment, a process as contemplated herein is exemplified by the application of a colorant (F) to the keratinous material, wherein the colorant (F) is an amino-functional silicone polymer of formula (Si-VII)

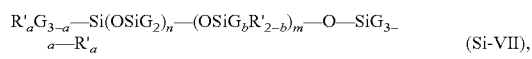

(Si-VII), wherein means:

G is-H, a phenyl group, —OH, —O—CH$_3$, —CH$_3$, —O—CH$_2$CH$_3$, —CH$_2$CH$_3$, —O—CH$_2$CH$_2$CH$_3$, —CH$_2$CH$_2$CH$_3$, —O—CH(CH$_3$)$_2$, —CH(CH$_3$)$_2$, —O—CH$_2$CH$_2$CH$_2$CH$_3$, —CH$_2$CH$_2$CH$_2$CH$_3$, —O—CH$_2$CH(CH$_3$)$_2$, —CH$_2$CH(CH$_3$)$_2$, —O—CH(CH$_3$)CH$_2$CH$_3$, —CH(CH$_3$)CH$_2$CH$_3$, —O—C(CH$_3$)$_3$, —C(CH$_3$)$_3$;

a stands for a number between 0 and 3, especially 0;

b stands for a number between 0 and 1, especially 1, m and n are numbers whose sum (m+n) is between 1 and 2000, preferably between 50 and 150, where n preferably assumes values from 0 to 1999 and in particular from 49 to 149 and m preferably assumes values from 1 to 2000, in particular from 1 to 10, R' is a monovalent radical selected from
—Q—N(R")—CH$_2$—CH$_2$—N(R")$_2$
—Q—N(R")$_2$ —Q—N⁺(R″)₃A⁻
—Q—N⁺H(R″)₂ A⁻
—Q—N⁺H₂(R″)A⁻
—Q—N(R″)—CH₂—CH₂—N⁺R″H₂A⁻,
where each Q is a chemical bond, —CH₂—, —CH₂—CH₂—, —CH₂CH₂CH₂—, —C(CH₃)₂—, —CH₂CH₂CH₂CH₂—, —CH₂C(CH₃)₂—, —CH(CH₃)CH₂CH₂—,
R″ represents identical or different radicals selected from the group consisting of —H, —phenyl, —benzyl, —CH₂—CH(CH₃)Ph, the C₁₋₂₀ alkyl radicals, preferably —CH₃, —CH₂CH₃, —CH₂CH₂CH₃, —CH(CH₃)₂, —CH₂CH₂CH₂H₃, —CH₂CH(CH₃)₂, —CH(CH₃)CH₂CH₃, —C(CH₃)₃, and A represents an anion preferably selected from chloride, bromide, iodide or meth sulfate.

In the context of a further preferred embodiment, a process as contemplated herein is exemplified by the application of a colorant (F) to the keratinous material, the colorant (F) comprising at least one amino-functional silicone polymer (F-1) of formula (Si-VIIa),

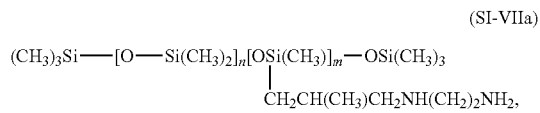

(SI-VIIa)

wherein m and n are numbers whose sum (m+n) is between 1 and 2000, preferably between 50 and 150, n preferably assuming values from 0 to 1999 and in particular from 49 to 149, and m preferably assuming values from 1 to 2000, in particular from 1 to 10.

According to the INCI declaration, these silicones are called trimethylsilylamodimethicones.

In the context of a further preferred embodiment, a process as contemplated herein is exemplified by the application of a colorant (F) to the keratinous material, the colorant (F) comprising at least one amino-functional silicone polymer of the formula (Si-VIIb)

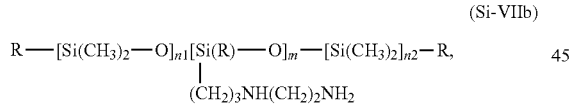

(Si-VIIb)

in which R represents —OH, —O—CH₃ or a —CH₃ group and m, n1 and n2 are numbers whose sum (m+n1+n2) is between 1 and 2000, preferably between 50 and 150, the sum (n1+n2) preferably assuming values from 0 to 1999 and in particular from 49 to 149 and m preferably assuming values from 1 to 2000, in particular from 1 to 10.

According to the INCI declaration, these amino-functionalized silicone polymers are called amodimethicones.

Regardless of which amino-functional silicones are used, colorants (F) as contemplated herein are preferred which contain an amino-functional silicone polymer whose amine number is above 0.25 meq/g, preferably above 0.3 meq/g and in particular above 0.4 meq/g. The amine number represents the milliequivalents of amine per gram of the amino-functional silicone. It can be determined by titration and also expressed in the unit mg KOH/g.

Furthermore, colorants (F) which include a special 4-morpholinomethyl-substituted silicone polymer (F-1) are also suitable for use in the process as contemplated herein. This amino-functionalized silicone polymer comprises structural units of the formulae (SI-VIII) and of the formula (Si-IX)

(Si-VIII)

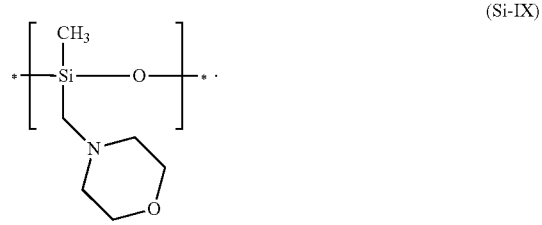

(Si-IX)

Corresponding 4-morpholinomethyl-substituted silicone polymers are described below.

A corresponding amino-functionalized silicone polymer is available under the name of Amodimethicone/Morpholinomethyl Silsesquioxane Copolymer is known and commercially available from Wacker in the form of the raw material Belsil ADM 8301 E.

As a 4-morpholinomethyl-substituted silicone, for example, a silicone can be used which has structural units of the formulae (Si-VIII), (Si-IX) and (Si-X)

(Si-VIII)

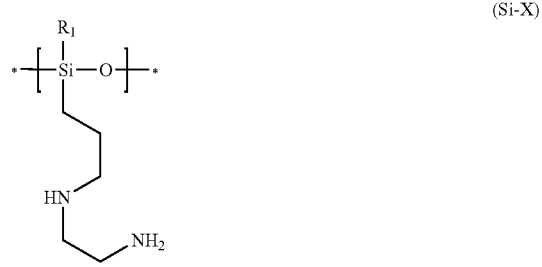

(Si-X)

(Si-IX)

in which
R1 is —CH₃, —OH, —OCH₃, —O—CH₂CH₃, —O—CH₂CH₂CH₃, or —O—CH(CH₃)₂;
R2 is —CH₃, —OH, or —OCH₃.

Particularly preferred colorants (F) as contemplated herein contain at least one 4-morpholinomethyl-substituted silicone of the formula (Si-XI)

(Si-XI)

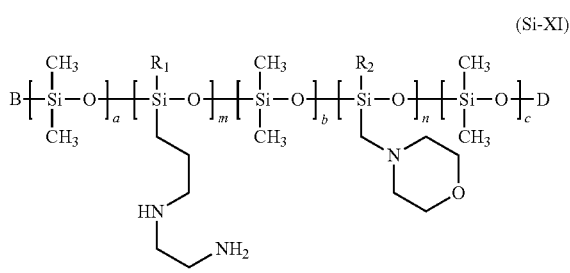

located in the
R1 is —$CH_3$, —OH, —$OCH_3$, —O—$CH_2CH_3$, —O—$CH_2CH_2CH_3$, or —O—$CH(CH_3)_2$;
R2 is —$CH_3$, —OH, or —$OCH_3$.
B represents a group —OH, —O—$Si(CH_3)_3$, —O—$Si(CH_3)_2OH$, —O—$Si(CH_3)_2OCH_3$,
D represents a group —H, —$Si(CH_3)_3$, —$Si(CH_3)_2OH$, —$Si(CH_3)_2OCH_3$,
a, b and c stand independently for integers between 0 and 1000, with the condition a+b+c>0
m and n independently of each other stand for integers between 1 and 1000
with the proviso that
at least one of the conditions B=—OH or D=—H is fulfilled,
the units a, b, c, m and n are distributed statistically or blockwise in the molecule.

Structural formula (Si-XI) is intended to illustrate that the siloxane groups n and m do not necessarily have to be directly bonded to a terminal grouping B or D, respectively. Rather, in preferred formulas (Si-VI) a>0 or b>0 and in particularly preferred formulas (Si-VI) a>0 and c>0, i.e. the terminal grouping B or D is preferably attached to a dimethylsiloxy grouping. Also in formula (Si-VI), the siloxane units a, b, c, m and n are preferably statistically distributed.

The silicones used as contemplated herein represented by formula (Si-VI) can be trimethylsilyl-terminated (D or B=—$Si(CH_3)_3$), but they can also be dimethylsilylhydroxy-terminated on two sides or dimethylsilylhydroxy-terminated and dimethylsilylmethoxy-terminated on one side. Silicones particularly preferred in the context of the present disclosure are selected from silicones in which
B=—O—$Si(CH_3)_2OH$ and D=—$Si(CH_3)_3$
B=—O—$Si(CH_3)_2OH$ and D=—$Si(CH_3)_2OH$
B=—O—$Si(CH_3)_2OH$ and D=—$Si(CH_3)_2OCH_3$
B=—O—$Si(CH_3)_3$ and D=—$Si(CH_3)_2OH$
B=—O—$Si(CH_3)_2OCH_3$ and D=—$Si(CH_3)_2OH$
These silicones lead to exorbitant improvements in the hair properties of the hair treated with the agents of the present disclosure, and to a seriously improved protection in oxidative treatment.

It has been found to be particularly advantageous if the colorant as contemplated herein comprises the amino-functionalized silicone polymer(s) (F-1) in certain ranges of amounts. Particularly good results were obtained when the colorant—based on the total weight of the colorant—included one or more amino-functionalized silicone polymers (F-1) in a total amount of 0.1 to 8.0 wt %, preferably 0.2 to 5.0 wt %, more preferably 0.3 to 3.0 wt % and most preferably 0.4 to 2.5 wt %.

Within the scope of a further particularly preferred embodiment, a process is characterized in that the colorant (F) comprises—based on the total weight of the colorant—one or more amino-functionalized silicone polymers (F-1) in a total amount of from 0.1 to 8.0 wt. %, preferably from 0.2 to 5.0 wt. %, more preferably from 0.3 to 3.0 wt. % and very particularly preferably from 0.4 to 2.5 wt. %.

Pigments (F-2) in the Colorant (F)

As a second constituent to the present disclosure, the colorant (F) used in the process as contemplated herein comprises at least one pigment.

Pigments within the meaning of the present disclosure are coloring compounds which have a solubility in water at 25° C. of less than 0.5 g/L, preferably less than 0.1 g/L, even more preferably less than 0.05 g/L. Water solubility can be determined, for example, by the method described below: 0.5 g of the pigment are weighed in a beaker. A beaker glass is added. Then one litre of distilled water is added. This mixture is heated to 25° C. for one hour while stirring on a magnetic stirrer. If undissolved components of the pigment are still visible in the mixture after this period, the solubility of the pigment is below 0.5 g/L. If the pigment-water mixture cannot be assessed visually due to the high intensity of the possibly finely dispersed pigment, the mixture is filtered. If a proportion of undissolved pigments remains on the filter paper, the solubility of the pigment is below 0.5 g/L.

Suitable color pigments can be of inorganic and/or organic origin.

In a preferred embodiment, a colorant (F) as contemplated herein is characterized in that it comprises at least one colorant compound (F-2) from the group of inorganic and/or organic pigments.

In a preferred embodiment, a colorant (F) as contemplated herein is characterized in that it comprises at least one inorganic and/or organic pigment (F-2).

Preferred color pigments are selected from synthetic or natural inorganic pigments. Inorganic color pigments of natural origin can be produced, for example, from chalk, ochre, umber, green earth, burnt Terra di Siena or graphite. Furthermore, black pigments such as iron oxide black, colored pigments such as ultramarine or iron oxide red as well as fluorescent or phosphorescent pigments can be used as inorganic color pigments.

Particularly suitable are colored metal oxides, hydroxides and oxide hydrates, mixed-phase pigments, sulfur-comprising silicates, silicates, metal sulfides, complex metal cyanides, metal sulfates, chromates and/or molybdates. In particular, preferred color pigments are black iron oxide (CI 77499), yellow iron oxide (CI 77492), red and brown iron oxide (CI 77491), manganese violet (CI 77742), ultramarine (sodium aluminum sulfo silicates, CI 77007, pigment blue 29), chromium oxide hydrate (CI77289), iron blue (ferric ferrocyanides, CI77510) and/or carmine (cochineal).

As contemplated herein, colored pearlescent pigments are also particularly preferred color pigments. These are usually mica- and/or mica-based and can be coated with one or more metal oxides. Mica belongs to the layer silicates. The most important representatives of these silicates are muscovite, phlogopite, paragonite, biotite, lepidolite and margarite. To produce the pearlescent pigments in combination with metal oxides, the mica, mainly muscovite or phlogopite, is coated with a metal oxide.

As an alternative to natural mica, synthetic mica coated with one or more metal oxides can also be used as pearlescent pigment. Especially preferred pearlescent pigments are based on natural or synthetic mica (mica) and are coated with one or more of the metal oxides mentioned above. The color of the respective pigments can be varied by varying the layer thickness of the metal oxide(s).

In a further preferred embodiment, a process as contemplated herein is characterized in that the colorant (F) comprises at least inorganic pigment (F-2) which is preferably selected from the group of colored metal oxides, metal hydroxides, metal oxide hydrates, silicates, metal sulfides, complex metal cyanides, metal sulfates, bronze pigments and/or from colored mica- or mica-based pigments coated with at least one metal oxide and/or a metal oxychloride.

In a further preferred embodiment, a process as contemplated herein is characterized in that the colorant (F) comprises at least one pigment selected from mica- or mica-based pigments which are reacted with one or more metal oxides selected from the group consisting of titanium dioxide (CI 77891), black iron oxide (CI 77499), yellow iron oxide (CI 77492), red and/or brown iron oxide (CI 77491, CI 77499), manganese violet (CI 77742), ultramarine (sodium aluminum sulfosilicates, CI 77007, Pigment Blue 29), chromium oxide hydrate (CI 77289), chromium oxide (CI 77288) and/or iron blue (ferric ferrocyanide, CI 77510).

Examples of particularly suitable color pigments are commercially available under the trade names Rona®, Colorona®, Xirona®, Dichrona® and Timiron® from Merck, Ariabel® and Unipure® from Sensient, Prestige® from Eckart Cosmetic Colors and Sunshine® from Sunstar.

Particularly preferred color pigments with the trade name Colorona® are, for example:
 Colorona Copper, Merck, MICA, CI 77491 (IRON OXIDES)
 Colorona Passion Orange, Merck, Mica, CI 77491 (Iron Oxides), Alumina
 Colorona Patina Silver, Merck, MICA, CI 77499 (IRON OXIDES), CI 77891 (TITANIUM DIOXIDE)
 Colorona RY, Merck, CI 77891 (TITANIUM DIOXIDE), MICA, CI 75470 (CARMINE)
 Colorona Oriental Beige, Merck, MICA, CI 77891 (TITANIUM DIOXIDE), CI 77491 (IRON OXIDES)
 Colorona Dark Blue, Merck, MICA, TITANIUM DIOXIDE, FERRIC FERROCYANIDE
 Colorona Chameleon, Merck, CI 77491 (IRON OXIDES), MICA
 Colorona Aborigine Amber, Merck, MICA, CI 77499 (IRON OXIDES), CI 77891 (TITANIUM DIOXIDE)
 Colorona Blackstar Blue, Merck, CI 77499 (IRON OXIDES), MICA
 Colorona Patagonian Purple, Merck, MICA, CI 77491 (IRON OXIDES), CI 77891 (TITANIUM DIOXIDE), CI 77510 (FERRIC FERROCYANIDE)
 Colorona Red Brown, Merck, MICA, CI 77491 (IRON OXIDES), CI 77891 (TITANIUM DIOXIDE)
 Colorona Russet, Merck, CI 77491 (TITANIUM DIOXIDE), MICA, CI 77891 (IRON OXIDES)
 Colorona Imperial Red, Merck, MICA, TITANIUM DIOXIDE (CI 77891), D&C RED NO. 30 (CI 73360)
 Colorona Majestic Green, Merck, CI 77891 (TITANIUM DIOXIDE), MICA, CI 77288 (CHROMIUM OXIDE GREENS)
 Colorona Light Blue, Merck, MICA, TITANIUM DIOXIDE (CI 77891), FERRIC FERROCYANIDE (CI 77510)
 Colorona Red Gold, Merck, MICA, CI 77891 (TITANIUM DIOXIDE), CI 77491 (IRON OXIDES)
 Colorona Gold Plus MP 25, Merck, MICA, TITANIUM DIOXIDE (CI 77891), IRON OXIDES (CI 77491)
 Colorona Carmine Red, Merck, MICA, TITANIUM DIOXIDE, CARMINE
 Colorona Blackstar Green, Merck, MICA, CI 77499 (IRON OXIDES)
 Colorona Bordeaux, Merck, MICA, CI 77491 (IRON OXIDES)
 Colorona Bronze, Merck, MICA, CI 77491 (IRON OXIDES)
 Colorona Bronze Fine, Merck, MICA, CI 77491 (IRON OXIDES)
 Colorona Fine Gold MP 20, Merck, MICA, CI 77891 (TITANIUM DIOXIDE), CI 77491 (IRON OXIDES)
 Colorona Sienna Fine, Merck, CI 77491 (IRON OXIDES), MICA
 Colorona Sienna, Merck, MICA, CI 77491 (IRON OXIDES)
 Colorona Precious Gold, Merck, Mica, CI 77891 (Titanium dioxide), Silica, CI 77491(Iron oxides), Tin oxide
 Colorona Sun Gold Sparkle MP 29, Merck, MICA, TITANIUM DIOXIDE, IRON OXIDES, MICA, CI 77891, CI 77491 (EU)
 Colorona Mica Black, Merck, CI 77499 (Iron oxides), Mica, CI 77891 (Titanium dioxide)
 Colorona Bright Gold, Merck, Mica, CI 77891 (Titanium dioxide), CI 77491(Iron oxides)
 Colorona Blackstar Gold, Merck, MICA, CI 77499 (IRON OXIDES)

Other particularly preferred color pigments with the trade name Xirona® are for example:
 Xirona Golden Sky, Merck, Silica, CI 77891 (Titanium Dioxide), Tin Oxide
 Xirona Caribbean Blue, Merck, Mica, CI 77891 (Titanium Dioxide), Silica, Tin Oxide
 Xirona Kiwi Rose, Merck, Silica, CI 77891 (Titanium Dioxide), Tin Oxide
 Xirona Magic Mauve, Merck, Silica, CI 77891 (Titanium Dioxide), Tin Oxide.

In addition, particularly preferred color pigments with the trade name Unipure® are for example:
 Unipure Red LC 381 EM, Sensient CI 77491 (Iron Oxides), Silica
 Unipure Black LC 989 EM, Sensient, CI 77499 (Iron Oxides), Silica
 Unipure Yellow LC 182 EM, Sensient, CI 77492 (Iron Oxides), Silica In a further embodiment, the pretreatment agent (V) as contemplated herein may also contain one or more organic pigments The organic pigments as contemplated herein are correspondingly insoluble, organic dyes or color lacquers, which may be selected, for example, from the group of nitroso, nitro-azo, xanthene, anthraquinone, isoindolinone, isoindolinone, quinacridone, perinone, perylene, diketo-pyrrolo-pyrrole, indigo, thioindido, dioxazine and/or triarylmethane compounds.

Examples of particularly suitable organic pigments are carmine, quinacridone, phthalocyanine, sorghum, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with the Color Index numbers CI 61565, CI 61570, CI 74260, orange pigments with the Color Index numbers CI 11725, CI 15510, CI 45370, CI 71105, red pigments with the Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

In another particularly preferred embodiment, a process as contemplated herein is characterized in that the colorant (F) comprises at least one organic pigment (F-2) which is preferably selected from the group consisting of carmine, quinacridone, phthalocyanine, sorghum, blue pigments having the Color Index numbers CI 42090, CI 69800, CI 69825, CI 73000, CI 74100, CI 74160, yellow pigments having the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915 and/or CI 75470.

The organic pigment can also be a color paint. As contemplated herein, the term color lacquer means particles comprising a layer of absorbed dyes, the unit of particle and dye being insoluble under the above mentioned conditions. The particles can, for example, be inorganic substrates, which can be aluminum, silica, calcium borosilate, calcium aluminum borosilicate or even aluminum.

For example, alizarin color varnish can be used.

Due to their excellent light and temperature resistance, the use of the above pigments in the colorant (F) of the process as contemplated herein is particularly preferred. It is also preferred if the pigments used have a certain particle size. As contemplated herein, it is therefore advantageous if the at least one pigment has an average particle size $D_{50}$ of 1.0 to 50 µm, preferably 5.0 to 45 µm, preferably 10 to 40 µm, in particular 14 to 30 µm. The average particle size $D_{50}$, for example, can be determined using dynamic light scattering (DLS).

The pigment(s) (F-2) constitute the second essential component of the colorant (F) as contemplated herein and are preferably used in the agent in certain ranges of amounts. Particularly good results were obtained when the colorant included—based on the total weight of the colorant—one or more pigments (F-2) in a total amount of 0.01 to 10.0 wt %, preferably 0.1 to 5.0 wt %, more preferably 0.2 to 2.5 wt % and most preferably 0.25 to 1.5 wt %.

In another very particularly preferred embodiment, a process as contemplated herein is characterized in that the colorant (F) comprises—based on the total weight of the colorant—one or more pigments (F-2) in a total amount of from 0.01 to 10.0 wt. %, preferably from 0.1 to 5.0 wt. %, more preferably from 0.2 to 2.5 wt. % and very particularly preferably from 0.25 to 1.5 wt. %.

Direct Dyes in the Colorant (F)

In principle, the colorants (F) used in the process of the present disclosure can also contain one or more direct-drawing colorants as optional components. Direct-acting dyes are dyes that draw directly onto the hair and do not require an oxidative process to form the color. Direct dyes are usually nitrophenylene diamines, nitroaminophenols, azo dyes, anthraquinones, triarylmethane dyes or indophenols.

The direct dyes within the meaning of the present disclosure have a solubility in water (760 mmHg) at 25° C. of more than 0.5 g/L and are therefore not to be regarded as pigments.

Preferably, the direct dyes within the meaning of the present disclosure have a solubility in water (760 mmHg) at 25° C. of more than 1.0 g/L.

However, the essential advantage of the process as contemplated herein is that the colorations obtainable with the pigment-based colorant (F) are, on the one hand, very wash-stable and, on the other hand, have a very high shade stability. This means that the fading of the coloration, if it occurs to a reduced extent after several washes of the keratin material, occurs while preserving the color nuance without any visible color shift. This shade stability is observed even when the colorant (F) comprises a mixture of pigments (F-2) of different colors.

Without being committed to this theory, it is assumed in this context that the reason for the high stability of the color shade is that all pigments are deposited in the form of a film on the surface of the keratin material. Unlike direct dyes, the pigments cannot diffuse into the keratin material, and also unlike direct dyes, the size or structure of a pigment cannot influence its penetration depth into the keratin material.

If a mixture of direct dyes of different colors is applied to the keratin material, these different dyes are usually based on different chromophoric structures and molecules of different sizes. Due to their structural differences, these different dyes can diffuse into the keratin material to different depths and are also washed out of the keratin material to different extents during washing. Particularly in the case of dyeing in natural shades, which are produced, for example, by using a mixture of a yellow, a red and a blue direct dye, a color shift from brown to yellowish, reddish or bluish can be observed over the course of several washes or shampoos.

The colorations produced via the process as contemplated herein are based on a pigment-silicone film localized on the surface of the keratin material. Washing tests have now shown that repeated washes do lead to a slight reduction in color intensity, but no shift in hue occurs. The dissolution of different colored pigments from the film during hair washing is therefore much more uniform.

The fact that this color shift does not occur when using the process as contemplated herein is a significant advantage over a dyeing system based on direct dyes. For this reason, it is particularly preferred if the colorant (F) does not contain any direct dyes or comprises them in only very small amounts.

In a further, very particularly preferred embodiment, a process as contemplated herein is characterized in that the total amount of direct dyes included in the colorant (F)—based on the total weight of the colorant (F)—is below 0.1 wt. %, preferably below 0.05 wt. %, more preferably below 0.01 wt. % and very particularly preferably below 0.001 wt. %.

In other words, in a further particularly preferred embodiment, a process as contemplated herein is characterized in that the total amount of the direct dyes included in the colorant (F)—based on the total weight of the colorant (F)—is below a value of 0.1 wt.- %, preferably below 0.05 wt. %, further preferably below 0.01 wt. % and very particularly preferably below 0.001 wt. %, the direct dyes being characterized in that they have a solubility in water (760 mmHg) at 25° C. of more than 0.5 g/L.

In a further, very particularly preferred embodiment, a process as contemplated herein is characterized in that the colorant (F) is free from direct dyes.

Direct dyes can be divided into anionic, cationic and non-ionic direct dyes.

Cationic direct dyes are, for example, Basic Blue 7, Basic Blue 26, HC Blue 16, Basic Violet 2 and Basic Violet 14, Basic Yellow 57, Basic Red 76, Basic Blue 16, Basic Blue 347 (Cationic Blue 347 / Dystar), HC Blue No. 16, Basic Blue 99, Basic Brown 16, Basic Brown 17, Basic Yellow 57, Basic Yellow 87, Basic Orange 31, Basic Red 51 Basic Red 76.

Examples of non-ionic direct dyes are nitro and quinone dyes and neutral azo dyes. Examples of nonionic direct dyes are those sold under the international designations or trade names HC Yellow 2, HC Yellow 4, HC Yellow 5, HC Yellow 6, HC Yellow 12, HC Orange 1, Disperse Orange 3, HC Red 1, HC Red 3, HC Red 10, HC Red 11, HC Red 13, HC Red BN, HC Blue 2, HC Blue 11, HC Blue 12, Disperse Blue 3, HC Violet 1, Disperse Violet 1, Disperse Violet 4, Disperse Black 9 known compounds, as well as 1,4-diamino-2-nitrobenzene, 2-amino-4-nitrophenol, 1,4-bis-(2-hydroxyethyl)-amino-2-nitrobenzene, 3-nitro-4-(2-hydroxyethyl)-aminophenol, 2-(2-hydroxyethyl)amino-4,6-dinitrophenol, 4-[(2-hydroxyethyl)amino]-3-nitro-1-methylbenzene, 1-amino-4-(2-hydroxyethyl)amino-5-chloro-2-nitrobenzene, 4-amino-3-nitrophenol, 1-(2'-ureidoethyl)amino-4-nitrobenzene, 2-[(4-amino-2-nitrophenyl)amino]-benzoic acid, 6-nitro-1,2,3,4-tetrahydroquinoxaline, 2-hydroxy-1,4-naphthoquinone, picramic acid and its salts, 2-amino-6-chloro-4-nitrophenol, 4-ethylamino-3-nitrobenzoic acid, and 2-chloro-6-ethylamino-4-nitrophenol.

Anionic direct dyes are also called acid dyes. Acid dyes are direct dyes that have at least one carboxylic acid group (—COOH) and/or one sulfonic acid group (—$SO_3H$). Depending on the pH value, the protonated forms (—COOH, —$SO_3H$) of the carboxylic acid or sulfonic acid groups are in equilibrium with their deprotonated forms (—$COO^-$, —$SO_3^-$ present). The proportion of protonated forms increases with decreasing pH. If direct dyes are used in the form of their salts, the carboxylic acid groups or sulfonic acid groups are present in deprotonated form and are neutralized with corresponding stoichiometric equivalents of cations to maintain electro neutrality. Inventive acid dyes can also be used in the form of their sodium salts and/or their potassium salts.

The acid dyes within the meaning of the present disclosure have a solubility in water (760 mmHg) at 25° C. of more than 0.5 g/L and are therefore not to be regarded as pigments. Preferably the acid dyes within the meaning of the present disclosure have a solubility in water (760 mmHg) at 25° C. of more than 1.0 g/L.

The alkaline earth salts (such as calcium salts and magnesium salts) or aluminum salts of acid dyes often have a lower solubility than the corresponding alkali salts. If the solubility of these salts is below 0.5 g/L (25° C., 760 mmHg), they do not fall under the definition of a direct dye.

An essential characteristic of acid dyes is their ability to form anionic charges, whereby the carboxylic acid or sulfonic acid groups responsible for this are usually linked to different chromophoric systems. Suitable chromophoric systems can be found, for example, in the structures of nitrophenylenediamines, nitroaminophenols, azo dyes, anthraquinone dyes, triarylmethane dyes, xanthene dyes, rhodamine dyes, oxazine dyes and/or indophenol dyes.

As examples of acid dyes can be mentioned: Acid Yellow 1 (D&C Yellow 7, Citronin A, Ext. D&C Yellow No. 7, Japan Yellow 403,CI 10316, COLIPA n° B001), Acid Yellow 3 (COLIPA n°: C 54, D&C Yellow N° 10, Quinoline Yellow, E104, Food Yellow 13), Acid Yellow 9 (CI 13015), Acid Yellow 17 (CI 18965), Acid Yellow 23 (COLIPA n° C. 29, Covacap Jaune W 1100 (LCW), Sicovit Tartrazine 85 E 102 (BASF), Tartrazine, Food Yellow 4, Japan Yellow 4, FD&C Yellow No. 5), Acid Yellow 36 (CI 13065), Acid Yellow 121 (CI 18690), Acid Orange 6 (CI 14270), Acid Orange 7 (2-Naphthol orange, Orange II, CI 15510, D&C Orange 4, COLIPA n° C.015), Acid Orange 10 (C.I. 16230; Orange G sodium salt), Acid Orange 11 (CI 45370), Acid Orange 15 (CI 50120), Acid Orange 20 (CI 14600), Acid Orange 24 (BROWN 1;CI 20170;KATSU201;nosodiumsalt;Brown No. 201;RESORCIN BROWN;ACID ORANGE 24;Japan Brown 201;D & C Brown No. 1), Acid Red 14 (C.I.14720), Acid Red 18 (E124, Red 18; CI 16255), Acid Red 27 (E 123, CI 16185, C-Rot 46, Real red D, FD&C Red Nr.2, Food Red 9, Naphthol red S), Acid Red 33 (Red 33, Fuchsia Red, D&C Red 33, CI 17200), Acid Red 35 (CI C.I.18065), Acid Red 51 (CI 45430, Pyrosin B, Tetraiodfluorescein, Eosin J, Iodeosin), Acid Red 52 (CI 45100, Food Red 106, Solar Rhodamine B, Acid Rhodamine B, Red n° 106 Pontacyl Brilliant Pink), Acid Red 73 (CI 27290), Acid Red 87 (Eosin, CI 45380), Acid Red 92 (COLIPA n° C.53, CI 45410), Acid Red 95 (CI 45425, Erythtosine,Simacid Erythrosine Y), Acid Red 184 (CI 15685), Acid Red 195, Acid Violet 43 (Jarocol Violet 43, Ext. D&C Violet n° 2, C.I. 60730, COLIPA n° C.063), Acid Violet 49 (CI 42640), Acid Violet 50 (CI 50325), Acid Blue 1 (Patent Blue, CI 42045), Acid Blue 3 (Patent Blue V, CI 42051), Acid Blue 7 (CI 42080), Acid Blue 104 (CI 42735), Acid Blue 9 (E 133, Patent Blue AE, Amido blue AE, Erioglaucin A, CI 42090, C.I. Food Blue 2), Acid Blue 62 (CI 62045), Acid Blue 74 (E 132, CI 73015), Acid Blue 80 (CI 61585), Acid Green 3 (CI 42085, Foodgreenl), Acid Green 5 (CI 42095), Acid Green 9 (C.I.42100), Acid Green 22 (C.I.42170), Acid Green 25 (CI 61570, Japan Green 201, D&C Green No. 5), Acid Green 50 (Brilliant Acid Green BS, C.I. 44090, Acid Brilliant Green BS, E 142), Acid Black 1 (Black n° 401, Naphthalene Black 10B, Amido Black 10B, CI 20 470, COLIPA n° B15), Acid Black 52 (CI 15711), Food Yellow 8 (CI 14270), Food Blue 5, D&C Yellow 8, D&C Green 5, D&C Orange 10, D&C Orange 11, D&C Red 21, D&C Red 27, D&C Red 33, D&C Violet 2 and/or D&C Brown 1.

For example, the water solubility of anionic direct dyes can be determined in the following way. 0.1 g of the anionic direct dye is placed in a beaker. An agitator is added. Then add 100 ml of water. This mixture is heated to 25° C. on a magnetic stirrer while stirring. It is stirred for 60 minutes. The aqueous mixture is then visually assessed. If there are still undissolved radicals, the amount of water is increased— for example in steps of 10 ml. Water is added until the amount of dye used is completely dissolved. If the dye-water mixture cannot be assessed visually due to the high intensity of the dye, the mixture is filtered. If a proportion of undissolved dyes remains on the filter paper, the solubility test is repeated with a higher quantity of water. If 0.1 g of the anionic direct dye dissolves in 100 ml water at 25° C., the solubility of the dye is 1.0 g/L.

Acid Yellow 1 is called 8-hydroxy-5,7-dinitro-2-naphthalenesulfonic acid disodium salt and has a solubility in water of at least 40 g/L (25° C.).

Acid Yellow 3 is a mixture of the sodium salts of mono- and sisulfonic acids of 2-(2-quinolyl)-1H-indene-1,3(2H)-dione and has a water solubility of 20 g/L (25° C.).

Acid Yellow 9 is the disodium salt of 8-hydroxy-5,7-dinitro-2-naphthalenesulfonic acid, its solubility in water is above 40 g/L (25° C.).

Acid Yellow 23 is the trisodium salt of 4,5-dihydro-5-oxo-1-(4-sulfophenyl)-4-((4-sulfophenyl)azo)-1H-pyrazole-3-carboxylic acid and readily soluble in water at 25° C.

Acid Orange 7 is the sodium salt of 4-[(2-hydroxy-1-naphthyl)azo]benzene sulfonate. Its water solubility is more than 7 g/L (25° C.).

Acid Red 18 is the trinatirum salt of 7-hydroxy-8-[(E)-(4-sulfonato-1-naphthyl)-diazenyl)]-1,3-naphthalene disulfonate and has a very high water solubility of more than 20 wt. %.

Acid Red 33 is the diantrium salt of 5-amino-4-hydroxy-3-(phenylazo)-naphthalene-2,7-disulphonate, its solubility in water is 2.5 g/L (25° C.).

Acid Red 92 is the disodium salt of 3,4,5,6-tetrachloro-2-(1,4,5,8-tetrabromo-6-hydroxy-3-oxoxanthen-9-yl)benzoic acid, whose solubility in water is indicated as greater than 10 g/L (25° C.).

Acid Blue 9 is the disodium salt of 2-({4-[N-ethyl(3-sulfonatobenzyl]amino]phenyl}{4-[(N-ethyl(3-sulfonatobenzyl)imino]-2,5-cyclohexadien-1-ylidene}methyl)- benzenesulfonate and has a solubility in water of more than 20 wt. % (25° C.).

Urther Optional Ingredients in The Agents (V) and/or (F)

In addition to the ingredients essential to the present disclosure already described, the pretreatment agent (V) and/or the colorant (F) may also contain other optional ingredients.

The agents may also contain other active ingredients, auxiliaries and additives, such as solvents; fatty ingredients such as $C_8$-$C_{30}$ fatty alcohols, $C_8$-$C_{30}$ fatty acid triglycerides, $C_8$-$C_{30}$ fatty acid monoglycerides, $C_8$-$C_{30}$ fatty acid diglycerides and/or hydrocarbons; polymers; structurants such as glucose, maleic acid and lactic acid, hair conditioning compounds such as phospholipids, for example lecitin and cephalism; perfume oils, dimethyl isosorbide and cyclodextrins; fiber structure-improving active ingredients, in particular mono-, di- and oligosaccharides such as glucose, galactose, fructose, fructose and lactose; dyes for coloring the product; anti-dandruff active ingredients such as piroctone olamine, zinc omadine and climbazole; amino acids and oligopeptides; protein hydrolysates on an animal and/or vegetable basis, as well as in the form of their fatty acid condensation products or optionally anionically or cationically modified derivatives; vegetable oils; light stabilizers and UV blockers; active ingredients such as panthenol, pantothenic acid, pantolactone, allantoin, pyrrolidinonecarboxylic acids and their salts, and bisabolol; Polyphenols, in particular hydroxycinnamic acids, 6,7-dihydroxycoumarins, hydroxybenzoic acids, catechins, tannins, leucoanthocyanidins, anthocyanidins, flavanones, flavones and flavonols; ceramides or pseudoceramides; vitamins, provitamins and vitamin precursors; plant extracts; Fats and waxes such as fatty alcohols, beeswax, montan wax and kerosenes; swelling and penetrating agents such as glycerol, propylene glycol monoethyl ether, carbonates, hydrogen carbonates, guanidines, ureas and primary, secondary and tertiary phosphates; opacifiers such as latex, styrene/PVP and styrene/acrylamide copolymers; pearlescing agents such as ethylene glycol mono- and distearate and PEG-3 distearate; and blowing agents such as propane-butane mixtures, $N_2O$, dimethyl ether, $CO_2$ and air.

The selection of these other substances will be made by the specialist according to the desired properties of the agents. With regard to other optional components and the quantities of these components used, explicit reference is made to the relevant manuals known to the specialist. The additional active ingredients and auxiliary substances are preferably used in the preparations as contemplated herein in quantities of 0.0001 to 25 wt. % each, in particular 0.0005 to 15 wt. %, based on the total weight of the respective agent.

pH Value of Pretreatment Agent (V) and/or Colorant (F)

The pH values of the agents (V) and (F) as contemplated herein can be adjusted to a slightly acidic to alkaline pH.

In one embodiment, the pretreatment agent (V) has a pH of from 6.0 to 12.0, preferably from 7.0 to 11.5, more preferably from 7.5 to 11.0, and most preferably from 9.0 to 11.0. If pretreatment agents (V) with these pH values were used in the process as contemplated herein, colorations with particularly good fastness properties could be obtained.

In a further embodiment, a process as contemplated herein is characterized in that the pretreatment agent (V) has a pH of from 6.0 to 12.0, preferably from 7.0 to 11.5, more preferably from 7.5 to 11.0, and most preferably from 9.0 to 11.0.

The pH values of the colorant (F) as contemplated herein can be adjusted to a slightly acidic to alkaline pH. Very preferably, colorant (F) has a pH in the range from 5.0 to 10.0, preferably from 6.0 to 9.5, more preferably from 6.0 to 8.7, and most preferably from 6.0 to 7.5.

Alkalizing agents and acidifying agents known to those skilled in the art can be used to set the respective desired pH values. The pH values for the purposes of the present disclosure are pH values measured at a temperature of 22° C.

As alkalizing agents, the agents may contain, for example, ammonia, alkanolamines and/or basic amino acids.

The alkanolamines which can be used in the agent of the present disclosure are preferably selected from primary amines having a $C_2$-$C_6$ alkyl base which carries at least one hydroxyl group. Preferred alkanolamines are selected from the group formed by 2-aminoethan-1-ol (monoethanolamine), 3-aminopropan-1-ol, 4-aminobutan-1-ol, 5-aminopentan-1-ol, 1-aminopropan-2-ol, 1-aminobutan-2-ol, 1-aminopentan-2-ol, 1-aminopentan-3-ol, 1-aminopentan-4-ol, 3-amino-2-methylpropan-1-ol, 1-amino-2-methylpropan-2-ol, 3-aminopropan-1,2-diol, 2-amino-2-methylpropan-1,3-diol.

Alkanolamines particularly preferred as contemplated herein are selected from 2-aminoethan-1-ol and/or 2-amino-2-methylpropan-1-ol. A particularly preferred embodiment is therefore characterized in that the agent as contemplated herein comprises an alkanolamine selected from 2-aminoethan-1-ol and/or 2-amino-2-methylpropan-1-ol as alkalizing agent.

For the purposes of the present disclosure, an amino acid is an organic compound comprising at least one protonatable amino group and at least one —COOH or —$SO_3H$ group in its structure. Preferred amino acids are aminocarboxylic acids, especially α-(alpha)-aminocarboxylic acids and ω-aminocarboxylic acids, whereby α-aminocarboxylic acids are particularly preferred.

As contemplated herein, basic amino acids are those amino acids which have an isoelectric point pI of greater than 7.0.

Basic α-aminocarboxylic acids contain at least one asymmetric carbon atom. In the context of the present disclosure, both possible enantiomers can be used equally as specific compounds or their mixtures, especially as racemates. However, it is particularly advantageous to use the naturally preferred isomeric form, usually in L-configuration.

The basic amino acids are preferably selected from the group formed by arginine, lysine, ornithine and histidine, especially preferably arginine and lysine. In another particularly preferred embodiment, an agent as contemplated herein is therefore characterized in that the alkalizing agent is a basic amino acid from the group arginine, lysine, ornithine and/or histidine.

In addition, the product may contain other alkalizing agents, especially inorganic alkalizing agents. Inorganic alkalizing agents usable as contemplated herein are preferably selected from the group formed by sodium hydroxide, potassium hydroxide, calcium hydroxide, barium hydroxide, sodium phosphate, potassium phosphate, sodium silicate, sodium metasilicate, potassium silicate, sodium carbonate and potassium carbonate.

Also as contemplated herein, the desired pH value can be adjusted by employing a buffer system. A buffer or buffer system is usually understood to be a mixture of a weak or medium-strength acid (e.g. acetic acid) with a practically completely dissociated neutral salt of the same acid (e.g. sodium acetate). If some base or acid is added, the pH value hardly changes (buffering). The effect of the buffer substances included in a buffer solution is based on the scavenging reaction of hydrogen or hydroxide ions with the formation of weak acids or bases due to their dissociation equilibrium. A buffer system can be formed from a mixture of an inorganic or organic acid and a corresponding salt of that acid. Acids can be buffered by all salts of weak acids and strong bases, bases by salts of strong acids and weak bases. The strong hydrochloric acid (completely dissociated into ions) can be buffered, for example, by adding sodium acetate. According to the balance

hydrochloric acid is converted by sodium acetate to the weak acetic acid with the formation of sodium chloride, which dissociates only to a very small extent in the presence of an excess of sodium acetate. Buffers that are effective against both acids and bases are mixtures of weak acids and their salts.

Examples of buffer systems known from the literature are acetic acid/sodium acetate, boric acid/sodium borate, phosphoric acid/sodium phosphate and hydrogen carbonate/soda.

The pH of the agent as contemplated herein can be adjusted, for example, by adding an inorganic or organic buffer system. For the purposes of the present disclosure, an inorganic buffer system is understood to be a mixture of an inorganic acid and its conjugate corresponding inorganic base.

For the purposes of the present disclosure, an organic buffer system is understood to be a mixture of an organic acid and its conjugate corresponding base. Due to the organic acid radical, the conjugate corresponding base of the organic acid is also organic. Here, the cation present to neutralize the charge of the acid anion can be inorganic or organic.

Examples of inorganic acids are sulfuric acid, hydrochloric acid and phosphoric acid ($H_3PO_4$). Phosphoric acid is a medium-strength acid that is particularly preferred.

A particularly well-suited inorganic acid is potassium dihydrogen phosphate Potassium dihydrogen phosphate has the molecular formula $KH_2PO_4$ and carries the CAS number 7778-77-0. Potassium dihydrogen phosphate has a molar mass of 136.09 g/mol. It is highly soluble in water (222 g/l at 20° C.) and reacts acidically in water. A 5% solution of potassium dihydrogen phosphate in water has a pH value of 4.4.

Another particularly suitable inorganic acid is sodium dihydrogen phosphate. Sodium dihydrogen phosphate has the molecular formula $NaH_2PO_4$ and carries the CAS numbers 7558-80-7 (anhydrate), 10049-21-5 (monohdate) and 13472-35-0 (dihydrate). The anhydrous sodium dihydrogen phosphate has a molar mass of 119.98 g/mol. Sodium dihydrogen phosphate reacts acidically in aqueous solution.

Particularly preferred as a corresponding salt of the above two acids is dipotassium hydrogen phosphate. Dipotassium hydrogen phosphate has the molecular formula $K_2HPO_4$ and carries the CAS numbers 7758-11-4 (anhydrous) and 16788-57-1 (trihydrate). The anhydrous dipotassium hydrogen phosphate has a molar mass of 174.18 g/mol. Dipotassium hydrogen phosphate reacts alkaline in aqueous solution.

Also particularly preferred as a corresponding salt of the above two acids is disodium hydrogen phosphate. Disodium hydrogen phosphate has the molecular formula $Na_2HPO_4$ and carries the CAS numbers 7558-79-4 (anhydrous), 10028-24-7 (dihydrate), 7782-85-6 (heptahydrate) and 10039-32-4 (dodecahydrate). Anhydrous disodium hydrogen phosphate has a molar mass of 141.96 g/mol. Disodium hydrogen phosphate reacts alkaline in aqueous solution.

Examples of organic acids are citric acid, succinic acid, tartaric acid, lactic acid, acetic acid, malic acid, malonic acid and maleic acid.

Examples of the corresponding salts of these organic acids are the sodium and potassium salts of citric acid, the sodium and potassium salts of succinic acid, the sodium and potassium salts of tartaric acid, sodium and potassium salts of lactic acid, sodium and potassium salts of acetic acid, sodium and potassium salts of malic acid, sodium and potassium salts of malonic acid and sodium and potassium salts of maleic acid.

Sequence of the Process Steps

As previously described, the pretreatment agent (V) is applied before the application of the colorant (F). In this context, it has been found to be particularly preferable to apply the pretreatment agent (V) to the keratin material, allow it to act for a certain period of time and then rinse it out again with water.

Accordingly, a further subject matter is a process for coloring keratinous fibers, in particular human hair, comprising the following steps in the order indicated:
(1) Applying a pretreatment agent (V) to the keratinous fibers, the pretreatment agent (V) having been disclosed in detail in the description of the first subject matter of the present disclosure,
(2) Exposure of the pretreatment agent applied in step (1) to the keratinous fibers for a period of 2 to 45 minutes, preferably 2 to 30 minutes and particularly preferably 2 to 20 minutes,
(3) Rinse out the pretreatment agent with water,
(4) Applying a colorant (F) to the keratinous fibers, the colorant having been disclosed in detail in the description of the first subject matter of the present disclosure,
(5) Exposing the colorant applied in step (4) to the keratinous fibers for a period of time ranging from 15 seconds to 45 minutes, preferably from 30 seconds to 30 minutes, and more preferably from 1 to 15 minutes, and
(6) Rinse out the dye with water.

In step (1) of the method as contemplated herein, a pretreatment agent (V) comprising at least one oxidizing agent in a water-comprising carrier is applied to the hair.

In the following step, the previously applied pretreatment agent (V) is allowed to act on the keratin fibers. In this context, various exposure times of 2 to 45 minutes, preferably 2 to 30 minutes and particularly preferably 2 to 20 minutes are possible.

Following the action of the pretreatment agent (V) on the keratin fibers, it is finally rinsed with water in step (3). In this case, the pretreatment agent (V) can either be washed out with water only, i.e. without the aid of a shampoo, or the washing-out process can be assisted by the application of a shampoo.

In principle, the user is now free to choose the period of time between the application of the two agents (V) and (F).

However, it may be preferred that no other agents, such as other conditioners, styling agents are applied between the application of the two agents (V) and (F). In this way, the maximum time interval between the application of the two agents (V) and (F) is preferably limited to a maximum of 24 hours.

It has been found to be preferable if between the rinsing of the pretreatment agent (V) with water and the application of a coloring agent (F) to the keratinous fibers there is a period of not more than 24 hours, preferably not more than 12 hours, further preferably not more than 6 hours and very particularly preferably not more than 3 hours.

In the context of a further preferred embodiment, a process as contemplated herein is characterized in that between steps (3) and (4) there is a period of time of at most 24 hours, preferably of at most 12 hours, further preferably of at most 6 hours and very particularly preferably of at most 3 hours.

In the context of a further preferred embodiment, a process as contemplated herein is characterized in that step (4) takes place directly after step (3). Step (4) is used to apply the colorant.

The exposure of the colorant (F) to the keratinous fibers in step (5) may be for a period of time ranging from 15 seconds to 30 minutes, for example, preferably for a period of time ranging from 30 seconds to 15 minutes, more preferably for a period of time ranging from 1 to 15 minutes.

After that, the colorant (F) is finally rinsed with water in step (6). Here, in a preferred embodiment, the colorant (F) is washed out with water only, i.e. without the aid of an after treatment agent or shampoo not as contemplated herein.

Multi-Component Packaging Unit

To increase user convenience, the user is preferably provided with all the necessary agents in the form of a multi-component packaging unit (kit-of-parts).

Thus, another object of the present disclosure is a multi-component packaging unit (kit-of-parts) for dyeing keratinous material, comprising separately prepared
- a first container comprising a pretreatment agent(V), the pretreatment agent(V) having been disclosed in detail in the description of the first subject matter of the present disclosure, and
- a second container comprising a colorant (F), the colorant (F) having been disclosed in detail in the description of the first subject matter of the present disclosure.

Concerning the further preferred embodiments of the multicomponent packaging unit as contemplated herein, mutatis mutantis what has been said about the processes as contemplated herein applies.

Use of The Dyeing Mixture (F) for Dyeing Oxidative Pretreated Hair

As previously described, with successive application of pretreatment agent (V) and dyeing agent (F), dyeing with greatly improved wash fastness and very good shade stability could be obtained. The oxidative pretreatment is seen as the cause of the improved durability of the colorant (F), i.e. the structural changes of the keratin material caused by the action of the oxidizing agents (V-1) seem to result in the film formed by the colorant (F) having improved adhesion to the surface of the keratin material (or hair fiber).

For the production of wash-stable dyeing on hair, the process of the first object of the present disclosure therefore has outstanding suitability. In addition, however, there is still the possibility that users who have previously subjected their hair to an oxidative treatment, such as hair bleaching or hair bleaching, may subsequently wish to change the color of the hair thus bleached once again. As has been shown, the colorant (F) as contemplated herein is also very suitable for this group of people.

Another object of the present disclosure is therefore the use of a coloring agent (F), as disclosed in detail in the description of the first object of the present disclosure, for coloring oxidative pretreated human hair.

Oxidative pre-treatment of the hair means the treatment of the hair with an oxidizing agent, usually commercially available bleaching or bleaching agents can be used for this purpose. These commercially available bleaching agents, which are well known to the skilled person, generally contain as oxidizing agent at least one oxidizing agent selected from the group consisting of hydrogen peroxide, ammonium peroxodisulfate, potassium peroxodisulfate and sodium peroxodisulfate.

Concerning the further preferred embodiments of the use as contemplated herein, mutatis mutantis what has been said about the methods as contemplated herein.

EXAMPLES

1. Formulations

The following ready-to-use pretreatment agent (V) was prepared (all data in wt % unless otherwise stated):

| Pretreatment agent (V) | (V) |
|---|---|
| Sodium silicate | 14.4 |
| Magnesium carbonate | 5.2 |
| Sodium hexametaphosphate | 0.08 |
| Degalan RG S hv (Evonic, Methyl methacrylate, methacrylic acid copolymer, INCI ACRYLATES COPOLYMER) | 0.4 |
| EDTA, disodium salt | 0.24 |
| Polyquaternium-4 | 0.2 |
| Aerosil 50 (Evonic, hydrophilic fumed silica) | 0.16 |
| Potassium peroxodisulfate | 12.8 |
| Ammonium peroxodisulfate | 4.0 |
| Dimethicone | 0.6 |
| Paraffinum Liquidum | 2.7 |
| Sodium benzoate | 0.24 |
| Dipicolinic acid | 0.06 |
| Disodium pyrophosphate | 0.06 |
| Potassium hydroxide (50% aqueous solution) | 0.114 |
| 1.2-propanediol | 0.3 |
| Etidronic acid (60% aqueous solution) | 0.15 |
| Cetearyl alcohol | 2.16 |
| Ceteareth-20 | 0.72 |
| Hydrogen peroxide (50% aqueous solution) | 11.0 |
| Water | ad 100 |

The following colorant (F) was prepared (all data in wt. % unless otherwise stated):

| Coloring agent (F) | F |
|---|---|
| Emulgade CM (BASF,Cetearyl Isononanoate, Ceteareth-29, Cetearyl alcohol, Glcerylstearate, Glycerin, Ceteareth-10, Cetyl palmitate | 0.6 |
| Cetyl alcohol | 0.6 |
| Stearyl alcohol | 0.6 |
| Phenoxyethanol | 0.9 |
| Sodium salicylate | 0.4 |
| 1.2-propanediol | 2.0 |
| Potassium dihydrogen phosphate | 0.34 |
| Disodium hydrogen phosphate | 0.72 |
| Xanthan gum | 1.6 |
| Unipure Red LC3071, organic pigment CI 15850 | 1.0 g |
| Dow Corning 2-8566 (Siloxanes and Silicones, 3-[(2-Aminoethyl)amino]-2-methylpropyl Me, Di-Me-Siloxane) | 1.0 g |
| Water | ad 100 |

2. Application on strands

First, the pretreatment agent (V) was applied to hair strands (Kerling company). For this purpose, 0.2 g of pretreatment agent (V) per gram of hair was applied to each strand, massaged in and left to act at room temperature for 30 minutes. Then the strands were rinsed with water. The coloring agent (F) was applied to the still damp hair directly afterwards. For this purpose, 0.2 g of colorant (F) per gram of hair strand was massaged in, left to act for 1 minute and then rinsed out again with water and dried.

A reference strand was treated directly with the colorant (F) without applying the pretreatment agent (V). Before application of the dye (F), the reference strand was only moistened with water, then the dye was applied according to the procedure described above.

The dried hair strands were measured colorimetrically with a colorimeter from Datacolor, type Spectraflash 450.

Subsequently, each dyed strand was subjected to 6 manual hair washes. For each hair wash, the strand was dampened, then a commercial shampoo (Schwarzkopf, Schauma 7 herbs) was massaged into the strand for 25 seconds (0.25 g of shampoo per gram of hair). The strand was then washed with lukewarm tap water for 30 seconds and dried.

After completion of the 6 hair washes, each strand was colorimetrically measured again.

The dE value used for the assessment of wash fastness is derived from the measured L*a*b* colorimetric values as follows:

$$dE=[(L_i-L_0)^2+(a_i-a_0)^2+(b_i-b_0)]^{1/2}$$

$L_0$, $a_0$ and $b_0$=Measured values of the dyed strand before washing $L_i$, $a_i$ and $b_i$=Measured values of the dyed strand after 6 hair washes

| For e.g.: | Procedure | | 0 hair washes | | | 6 hair washes | | | |
|---|---|---|---|---|---|---|---|---|---|
| | (V) | (F) | $L_0$ | $a_0$ | $b_0$ | $L_i$ | $a_i$ | $b_i$ | dE |
| 1 Comparison | — | (F) | 47.18 | 7.11 | 19.31 | 33.05 | 25.50 | 12.02 | 24.31 |
| 2 Invention | (V) | (F) | 34.44 | 48.44 | 15.84 | 36.04 | 43.81 | 12.79 | 5.77 |

Example 1 is the comparative example in which the colorant (F) was applied without performing any pretreatment.

Example 2 is the example as contemplated herein with successive application of pretreatment agent (V) and colorant (F).

When the process as contemplated herein was applied, a greatly reduced dE value and consequently a greatly improved wash fastness was observed.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

What is claimed is:

1. A process for dyeing keratinous material comprising:
applying a pre-treatment agent (V) to the keratinous material, wherein the pre-treatment agent in a cosmetic carrier comprises at least one oxidizing agent (V-1),
after applying the pre-treatment agent (V) to the keratinous material, exposing the pretreatment agent to the keratinous fibers for a period of 2 to 45 minutes;
rinsing out the pretreatment agent with water;
after rinsing out the pretreatment, applying a colorant (F) to the keratinous material, the colorant being in a cosmetic carrier and comprising (F-1) at least one amino-functionalized silicone polymer and (F-2) at least one pigment;
exposing the colorant to the keratinous fibers for a period of from 15 seconds to 45 minutes, and
rinsing out the colorant with water.

2. A process for dyeing human hair comprising:
applying a pre-treatment agent (V) in a first cosmetic carrier to the human hair, wherein the pre-treatment agent comprises at least one oxidizing agent (V-1), and
applying a colorant (F) in a second cosmetic carrier to the human hair, wherein the colorant comprises at least one amino-functionalized silicone polymer (F-1) and at least one pigment (F-2), wherein the at least one oxidizing agent (V-1) is selected from the group consisting of hydrogen peroxide, ammonium peroxodisulfate, potassium peroxodisulfate and sodium peroxodisulfate.

3. The process according to claim 1, wherein the pretreatment agent (V) comprises (V-1) hydrogen peroxide and (V-2) at least one persulfate selected from the group consisting of ammonium peroxodisulfate, potassium peroxodisulfate and sodium peroxodisulfate.

4. The process according to claim 1, wherein the pretreatment agent (V)—based on the total weight of the pretreatment agent—comprises 0.1 to 12.0 wt. % of (V-1) hydrogen peroxide.

5. The process according to claim 1, wherein the pretreatment agent (V)—based on the total weight of the pretreatment agent—comprises (V-2) one or more persulfates selected from the group consisting of ammonium peroxodisulfate, potassium peroxodisulfate and sodium peroxodisulfate in a total amount of from 5.0 to 30.0 wt %.

6. The process according to claim 1, wherein the colorant (F) comprises at least one amino-functionalized silicone polymer (F-1) having at least one secondary amino group.

7. The process according to claim 1, wherein the colorant (F) comprises at least one amino-functionalized silicone polymer (F-1) comprising at least one structural unit of the formula (Si amino),

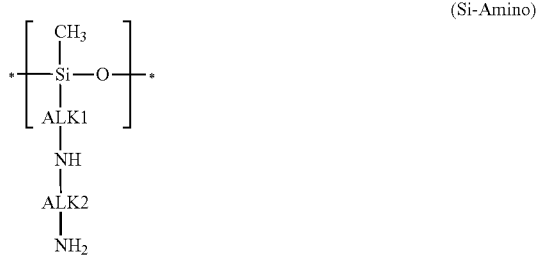
(Si-Amino)

where
ALK1 and ALK2 independently represent a linear or branched $C_1$-$C_{20}$ divalent alkylene group.

8. The process according to claim 1, wherein the colorant (F) comprises at least one amino-functionalized silicone polymer (F-1) comprising structural units of the formula (Si-I) and of the formula (Si-II)

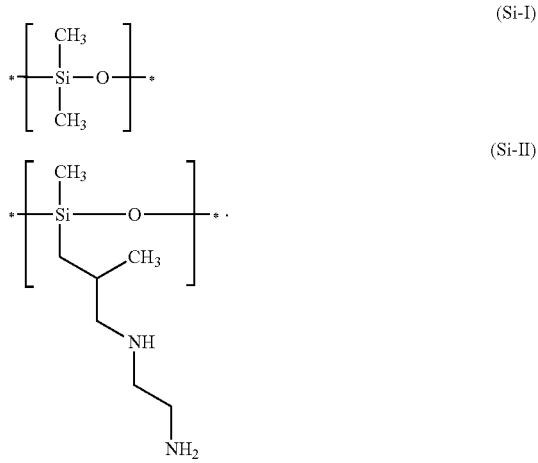

9. The process according to claim 1, wherein the colorant (F) comprises—based on the total weight of the colorant—one or more amino-functionalized silicone polymers (F-1) in a total amount of from 0.1 to 8.0 wt. %.

10. The process according to claim 1, wherein the colorant (F) comprises at least inorganic pigment (F-2) selected from the group consisting of colored metal oxides, metal hydroxides, metal oxide hydrates, silicates, metal sulfides, complex metal cyanides, metal sulfates, bronze pigments, and/or from mica- or mica-based colored pigments coated with at least one metal oxide and/or a metal oxychloride.

11. The process according to claim 1, wherein the colorant (F) comprises at least one organic pigment (F-2) selected from the group consisting of carmine, quinacridone, phthalocyanine, Sorgho, blue pigments with the Color Index numbers CI 42090, CI 69800, CI 69825, CI 73000, CI 74100, CI 74160, yellow pigments with the Color Index numbers CI 11680, CI 11710, CI 15985, CI 19140, CI 20040, CI 21100, CI 21108, CI 47000, CI 47005, green pigments with Color Index numbers CI 61565, CI 61570, CI 74260, orange pigments with Color Index numbers CI 11725, CI 15510, CI 45370, CI 71105, red pigments with Color Index numbers CI 12085, CI 12120, CI 12370, CI 12420, CI 12490, CI 14700, CI 15525, CI 15580, CI 15620, CI 15630, CI 15800, CI 15850, CI 15865, CI 15880, CI 17200, CI 26100, CI 45380, CI 45410, CI 58000, CI 73360, CI 73915, and/or CI 75470.

12. The process according to claim 1, wherein the colorant (F) comprises—based on the total weight of the colorant—one or more pigments (F-2) in a total amount of from 0.01 to 10.0 wt. %.

13. The process according to claim 1, wherein the colorant (F) comprises direct dyes, and wherein the total amount of direct dyes contained in the colorant (F) based on the total weight of the colorant (F)—is below 0.1 wt. %.

14. The process according to claim 1, further comprising waiting for a period of at most 24 hours after rinsing out the pretreatment agent with water before applying the colorant (F) to the keratinous material.

15. The process of claim 1, wherein the keratinous material is oxidative pretreated human hair.

16. A process for dyeing keratinous material comprising:
applying a pre-treatment agent (V) to the keratinous material, wherein the pre-treatment agent in a cosmetic carrier comprises at least one oxidizing agent (V-1), and wherein the pretreatment agent (V)—based on the total weight of the pretreatment agent—comprises 3.0 to 6.0 wt. % of (V-1) hydrogen peroxide; rinsing out the pretreatment agent (V) with water and
applying a colorant (F) to the keratinous material, the colorant being in a cosmetic carrier and comprising (F-1) at least one amino-functionalized silicone polymer and (F-2) at least one pigment.

17. The process according to claim 16, wherein the pretreatment agent (V)—based on the total weight of the pretreatment agent—comprises (V-2) one or more persulfates selected from the group consisting of ammonium peroxodisulfate, potassium peroxodisulfate and sodium peroxodisulfate in a total amount of from 14.0 to 21.0 wt %.

18. The process according to claim 17, wherein:
the keratinous material is oxidative pretreated human hair;
the colorant (F) comprises—based on the total weight of the colorant—one or more pigments (F-2) in a total amount of from 0.25 to 1.5 wt. %;
the colorant (F) comprises direct dyes;
the total amount of direct dyes contained in the colorant (F)—based on the total weight of the colorant (F)—is below 0.001 wt. %;
the colorant (F) comprises—based on the total weight of the colorant—one or more amino-functionalized silicone polymers (F-1) in a total amount of from 0.4 to 2.5 wt. %; and
the colorant (F) comprises at least inorganic pigment (F-2) selected from the group consisting of colored metal oxides, metal hydroxides, metal oxide hydrates, silicates, metal sulfides, complex metal cyanides, metal sulfates, bronze pigments, and/or from mica- or mica-based colored pigments coated with at least one metal oxide and/or a metal oxychloride.

19. The process according to claim 1, further comprising waiting for a period of at most 3 hours after rinsing out the pretreatment agent with water before applying the colorant (F) to the keratinous material.

20. The process according to claim 2 wherein:
the pretreatment agent (V), based on the total weight of the pretreatment agent, comprises 0.1 to 12.0 wt. % of (V-1) hydrogen peroxide; and the pretreatment agent (V), based on the total weight of the pretreatment agent, comprises 5.0 to 30.0 wt % of (V-2) at least one persulfate selected from the group consisting of ammonium peroxodisulfate, potassium peroxodisulfate and sodium peroxodisulfate.

* * * * *

UNITED STATES PATENT AND TRADEMARK OFFICE
CERTIFICATE OF CORRECTION

| | | |
|---|---|---|
| PATENT NO. | : 12,109,298 B2 | Page 1 of 1 |
| APPLICATION NO. | : 17/913725 | |
| DATED | : October 8, 2024 | |
| INVENTOR(S) | : Constanze Kruck et al. | |

It is certified that error appears in the above-identified patent and that said Letters Patent is hereby corrected as shown below:

In the Specification

Column 23, Line 18 change "Urther optional ingredients in the agents (V) and/or (F)" to --Further optional ingredients in the agents (V) and/or (F)--.
Column 26, Line 10 change "K2HP04" to --$K_2HPO_4$--.
Column 26, Line 17 change "Na2HPO4" to --$Na_2HPO_4$--.

Signed and Sealed this
Twenty-fifth Day of February, 2025

Coke Morgan Stewart
*Acting Director of the United States Patent and Trademark Office*